US005882310A

United States Patent [19]

Marian, Jr.

[11] Patent Number: 5,882,310

[45] Date of Patent: Mar. 16, 1999

[54] ULTRASOUND TRANSDUCER CONNECTOR AND MULTIPORT IMAGING SYSTEM RECEPTACLE ARRANGEMENT

[75] Inventor: Vaughn R. Marian, Jr., Saratoga, Calif.

[73] Assignee: Acuson Corporation, Mountain View, Calif.

[21] Appl. No.: 980,833

[22] Filed: Dec. 1, 1997

[51] Int. Cl.[6] ........ A61B 8/00

[52] U.S. Cl. ........ 600/459

[58] Field of Search ........ 600/437, 459; 73/628, 607

[56] References Cited

U.S. PATENT DOCUMENTS

| | | | |
|---|---|---|---|
| 4,726,230 | 2/1988 | Yoshikawa et al. | 73/607 |
| 4,811,740 | 3/1989 | Ikeda et al. | 600/437 |
| 5,205,175 | 4/1993 | Garza et al. | 600/437 |
| 5,308,252 | 5/1994 | Mroczkowski et al. . | |
| 5,318,027 | 6/1994 | Fukui | 600/437 |
| 5,617,866 | 4/1997 | Marian, Jr. . | |

FOREIGN PATENT DOCUMENTS

| | | |
|---|---|---|
| 97/13300 | 4/1997 | WIPO . |

*Primary Examiner*—George Manuel
*Attorney, Agent, or Firm*—Ladas & Parry

[57] ABSTRACT

A plurality of ultrasound imaging system receptacles are arranged either vertically one above the other or horizontally side-by-side, each receptacle having an insertion slot for receiving the contact pads of an inserted ultrasound transducer connector. All of a number of connectors may be inserted into corresponding receptacles, and the system functions to mutually exclusively engage a single receptacle with its inserted connector. An electrical circuit arrangement is provided for automatically sensing the transducer in use without an operator having to make the selection manually. An interconnect and actuation scheme permits the multiport connector/receptacle arrangement to be manufactured at low cost. The modest size of the connectors and the receptacle assembly allows their placement at convenient locations on the system, and the simple basic design of the connector allows for submersion in liquid disinfectants.

38 Claims, 21 Drawing Sheets

FIG. 5
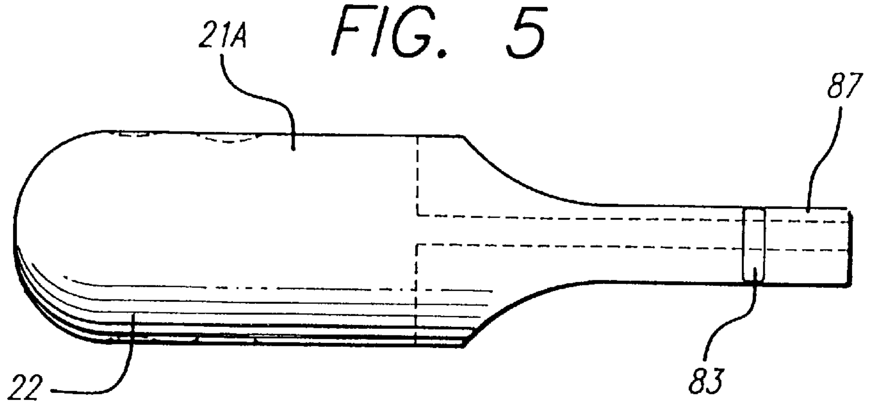
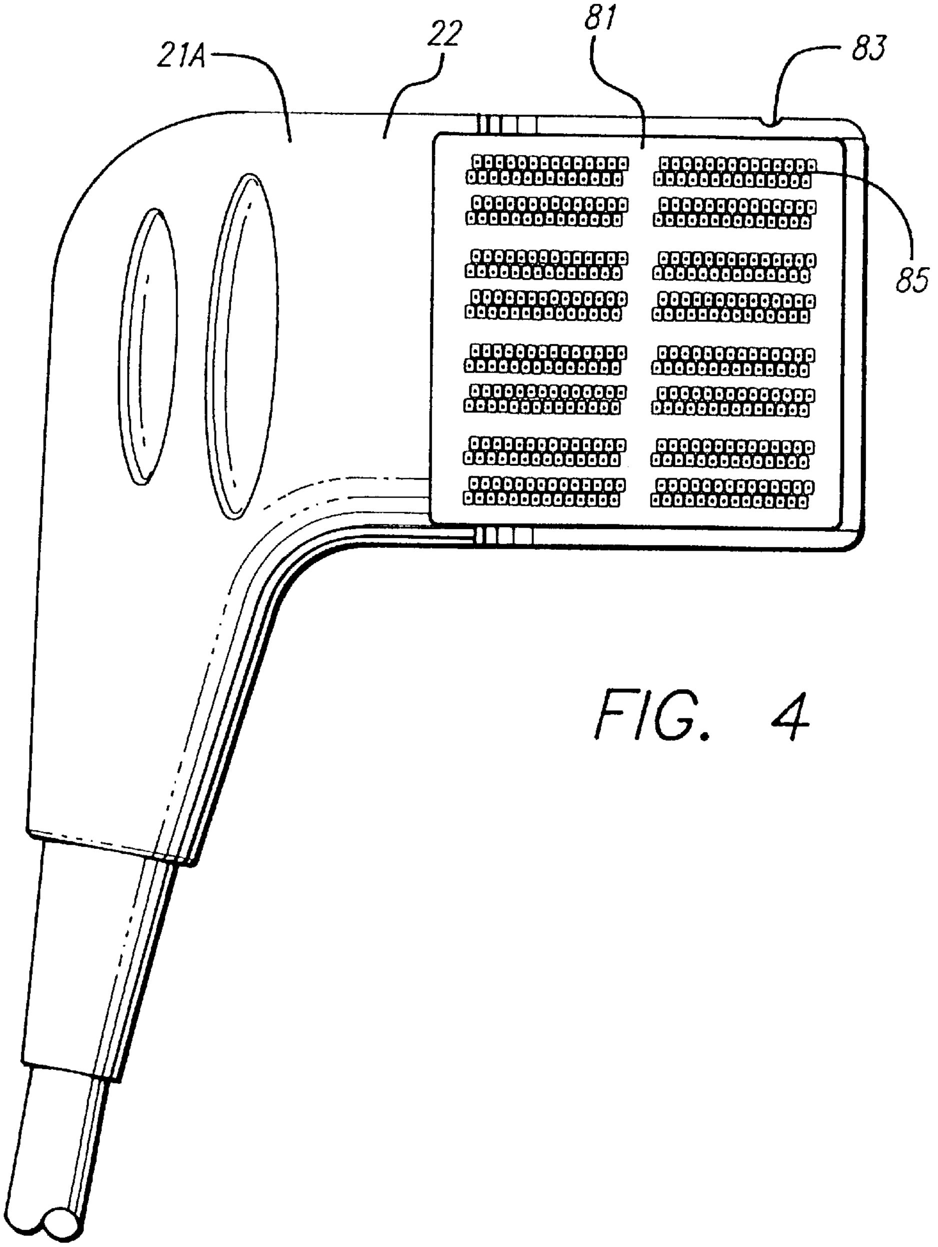
FIG. 4

FIG. 8
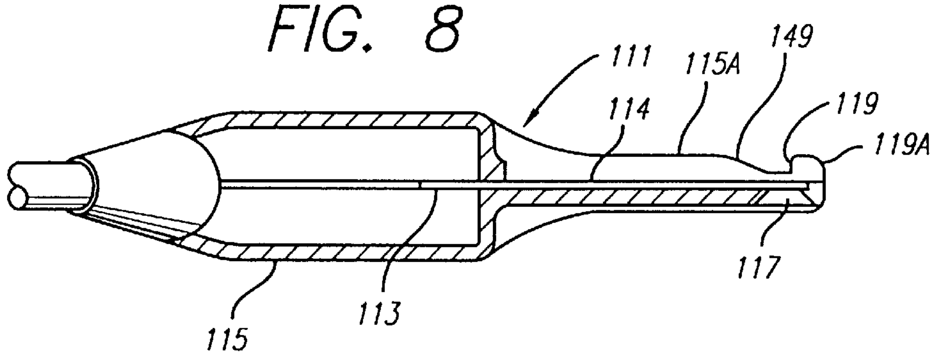
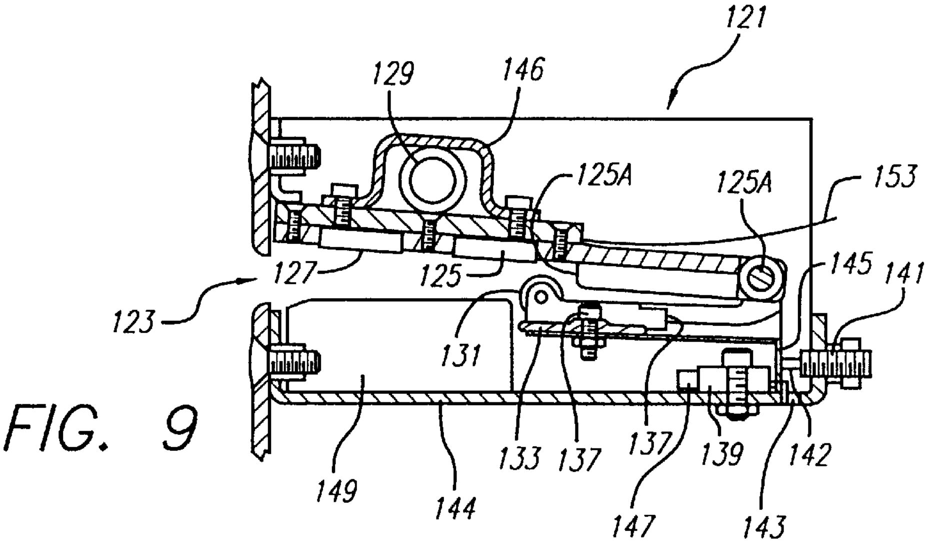
FIG. 9
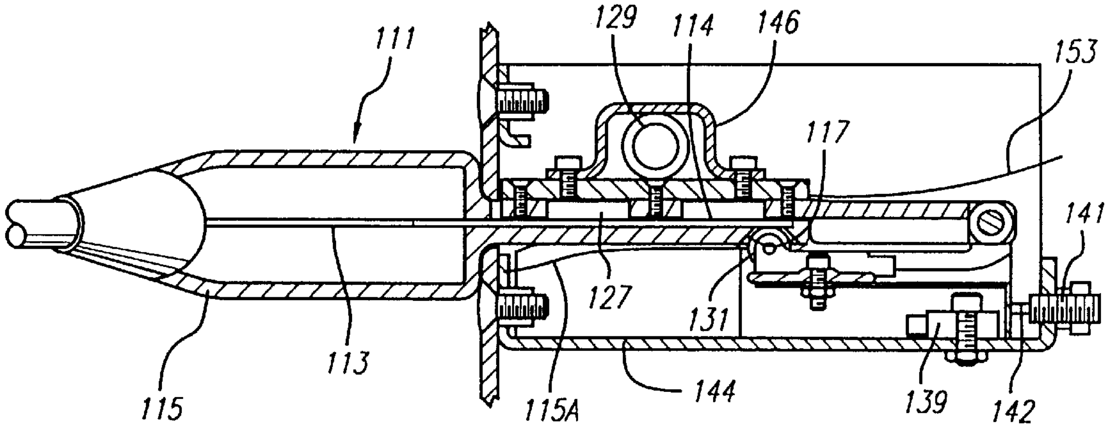
FIG. 10

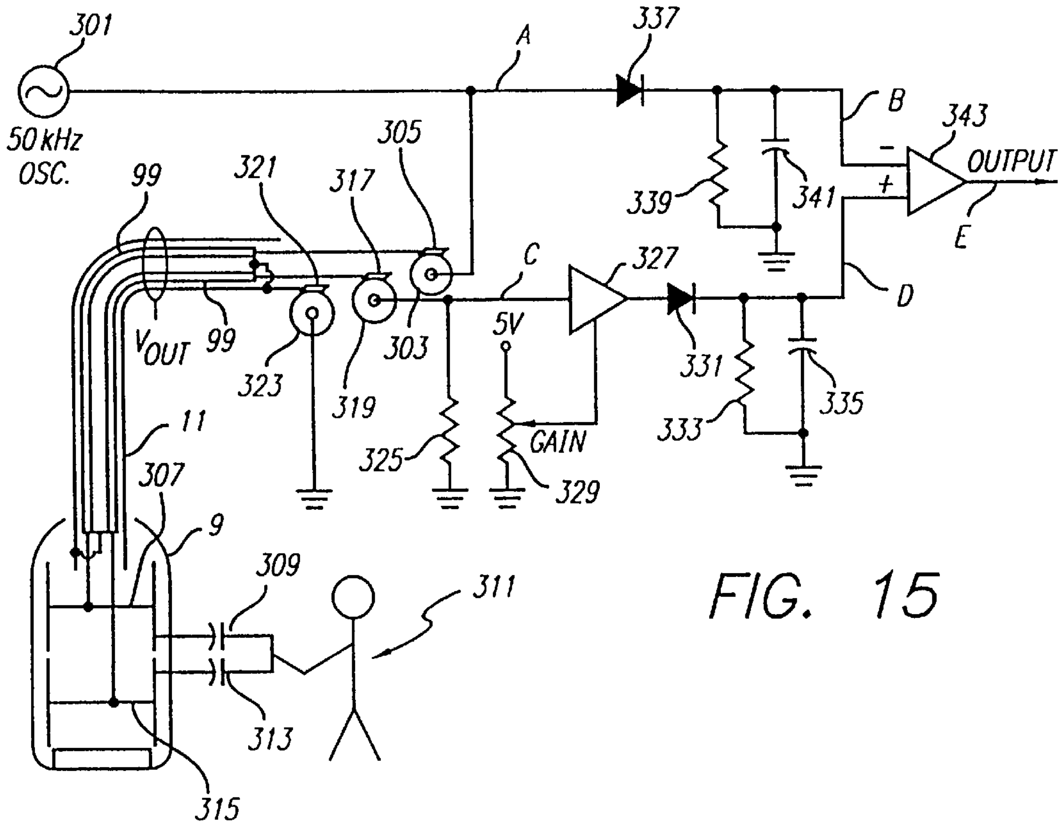
FIG. 15
FIG. 16
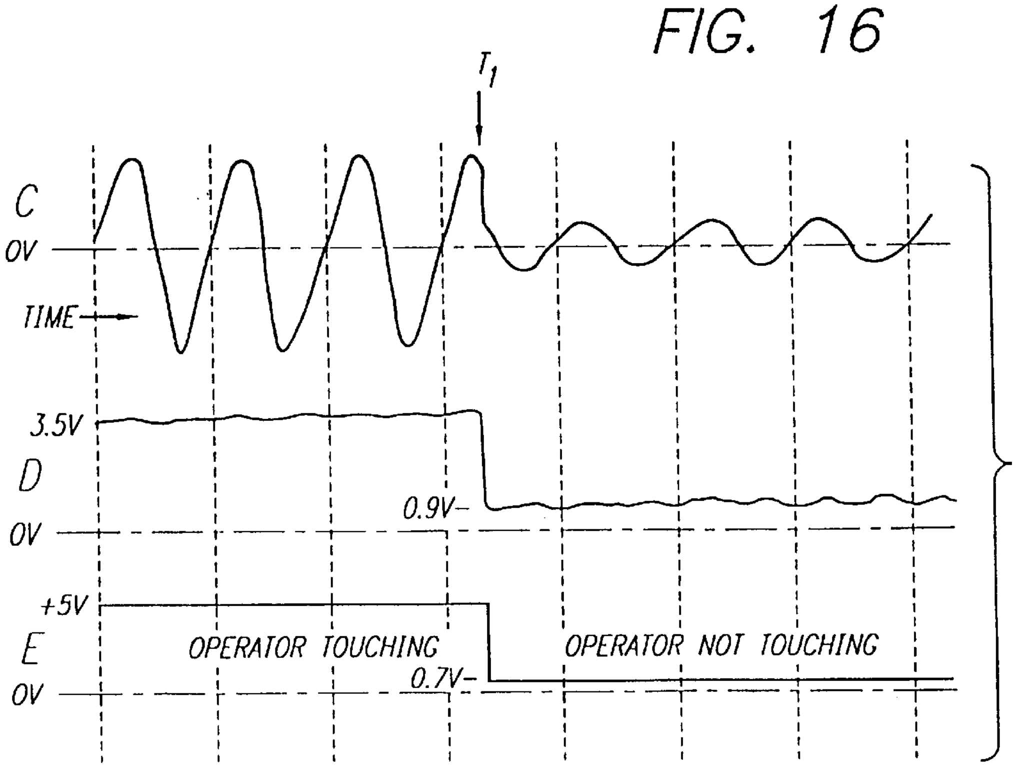

ULTRASOUND TRANSDUCER CONNECTOR AND MULTIPORT IMAGING SYSTEM RECEPTACLE ARRANGEMENT

BACKGROUND OF THE INVENTION

1. Field of the Invention

This invention relates to the field of ultrasound transducers, and in particular to an improved ultrasound transducer connector and multiport imaging system receptacle assembly of an ultrasound imaging system.

2. Brief Description of the Prior Art

Prior art imaging systems have included receptacles for two or three different transducer types. That is, two or three transducers are plugged into the system at any one time, and the selection of the transducer which is to be active is under control of the imaging system in response to operator input. The receptacles are normally located in the lower front face of the system because of its close proximity to the printed wiring board card cage assembly within the system console.

Existing transducer connectors which have a 256 channel (and higher) capacity are large, clumsy, expensive, and not submersible in fluids for cleaning and sterilization. The corresponding system receptacles are expensive and, in general located on the lower front surface of the imaging system because that location is in proximity to the electronics. This location is not the most convenient one for the operator, however. The industrial designer has little latitude in locating these receptacles.

Switching between transducers is accomplished in the prior art with electrically operated reed relays or FET switches (one for each channel and auxiliary function) which are expensive and inherently require a significant quantity of printed wiring board real estate.

There is thus a need in the art for a multiport connector and receptacle arrangement in which the transducer in use may be automatically selected without need for reed relays or FET switches, and in which the receptacles may be located in a more convenient location for the operator, which has other important operating features yet is lower in cost, and which employs submersible transducer connectors. The present invention fulfills these needs.

SUMMARY OF THE INVENTION

The present invention overcomes the deficiencies and inconveniences of the prior art by providing low cost submersible transducer connectors and compatible receptacles, allowing the ultrasound transducer to be strongly influenced by ergonomics. Because of the small size of the connectors and of the receptacles, the receptacles can be placed up high on the imaging system without compromising the desired electrical performance. This allows the operator to conveniently change transducers without bending over. A high location for the transducer connector and for the transducer holder minimizes the chance for system wheel/transducer cable interactions which are normally to the detriment of the cable.

The submersible transducer connector of the present invention is very simple and has no moving parts resulting in a low cost connection scheme. It is significantly less expensive to manufacture than existing connectors, and since each system uses four to five transducers, this savings can be quite significant.

The receptacle assembly is relatively simple and modular, even though it can accommodate three transducers at one time. The imaging system cost is significantly less than one based on prior art technology. This savings takes into account the elimination of transducer selection switches, the relatively expensive connector receptacles, and the elimination of safety doors, etc. The system of the present invention will allow an imaging system to be designed with reduced bulk and weight when compared to existing approaches; this aspect of the invention is very appealing to potential users.

In accordance with the invention, there is provided an ultrasound transducer connector and multiport ultrasound imaging system receptacle arrangement comprising a plurality of receptacles each having a set of receptacle contacts, a plurality of connectors each having a set of connector contacts, and an engagement actuator for automatically contacting only one of the set of receptacle contacts with the set of connector contacts of an inserted connector.

In another aspect of the invention, there is provided an ultrasound transducer connector and multiport ultrasound imaging system receptacle arrangement comprising a plurality of receptacles each having a set of receptacle contacts, the contacts of all receptacles being connected in parallel. A plurality of ultrasound transducer connectors are provided, each having a set of connector contacts arranged to electrically contact a corresponding set of receptacle contacts when the connector is received in, and engaged by, one of the receptacles. A connector selector exclusively engages the set of connector contacts of any one of the connectors with the set of receptacle contacts of the receptacle into which it is inserted.

In yet another aspect of the invention, there is provided an ultrasound transducer connector and multiport ultrasound imaging system receptacle arrangement comprising a plurality of receptacles each having a set of receptacle contacts, and a plurality of transducers each having a connector with a set of connector contacts. The plurality of connectors are insertable into the plurality of receptacles without mutually engaging the receptacle contacts with the connector contacts. An actuator, responsive to a transducer being used, engages the set of connector contacts of the transducer being used with the receptacle contacts of the receptacle into which the connector of the transducer being used is inserted.

BRIEF DESCRIPTION OF THE DRAWING

These and other aspects of the invention will be better understood, and additional features of the invention will be described hereinafter having reference to the accompanying drawings in which:

FIG. 4 is a side elevational view of the connector end of a portable transducer, the connector having a plurality of contact pads on one of its vertical faces for making contact with a corresponding set of contact pads of a receptacle into which the connector is inserted;

FIG. 5 is a top view of the connector of FIG. 4;

FIG. 8 is a partial cross view of another embodiment of a connector according to the present invention, the connector having a connector extension for insertion into a receptacle slot;

FIG. 9 is a partial cross-sectional view of a receptacle for receiving the connector of FIG. 8, the receptacle being shown in an unlocked condition;

FIG. 10 is a partial cross view of the connector of FIG. 8 inserted into the receptacle of FIG. 9, and with the receptacle in the locked condition;

FIG. 15 is a schematic diagram showing electrical connections for an automatically sensed transducer in use;

FIG. 16 is a timing diagram of the relationship between certain signals in the schematic of FIG. 15, showing the output signal with the operator touching a transducer and, alternatively, with the operator not touching the transducer;

DETAILED DESCRIPTION OF THE PREFERRED EMBODIMENTS

Figure 1:
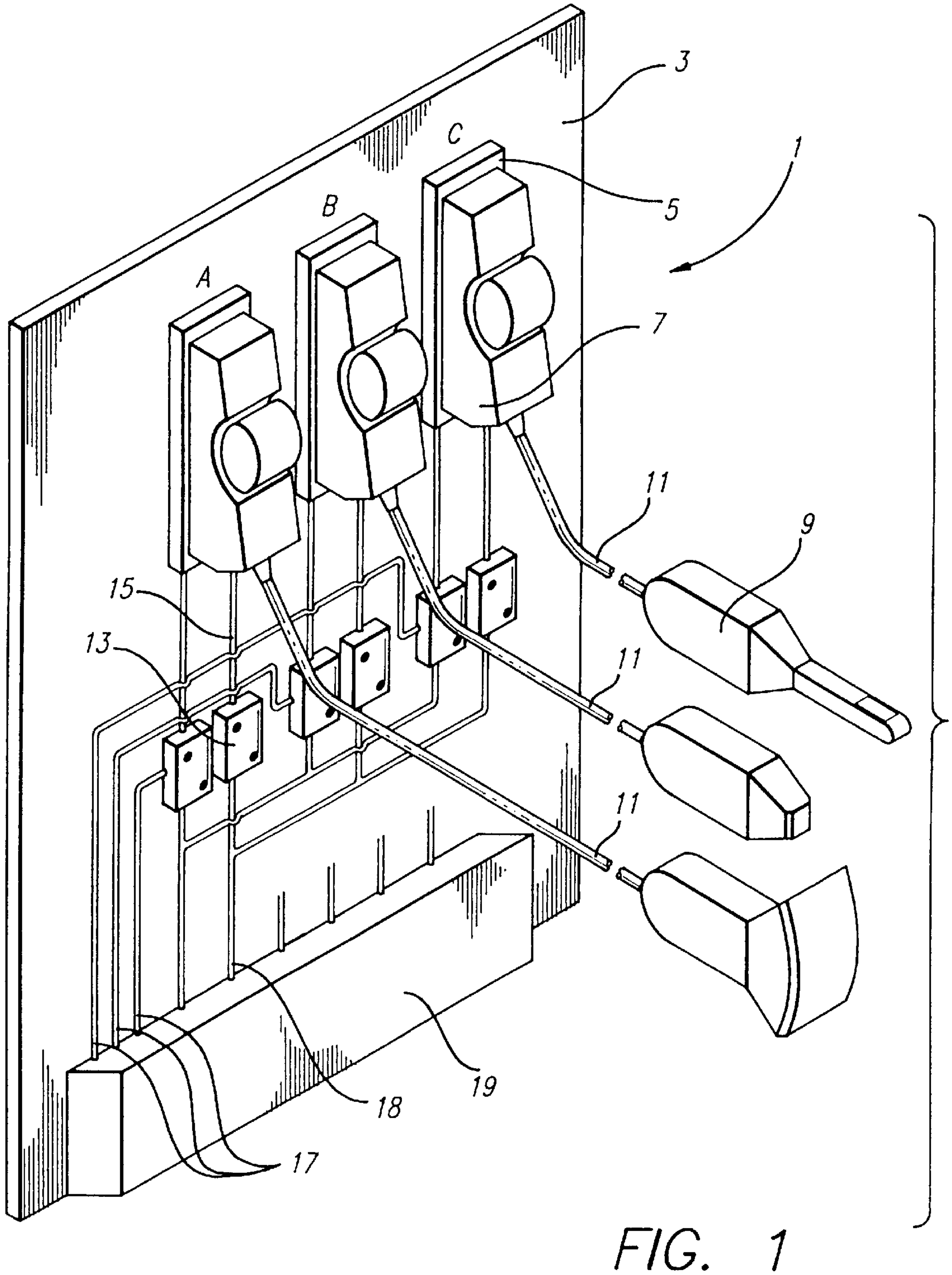
FIG. 1 PRIOR ART
FIG. 1 is a perspective view of a prior art imaging system transducer connection panel showing three ultrasound transducer connectors plugged into a corresponding number of receptacles on the panel.

FIG. 1 shows a typical prior art imaging system transducer connection panel 1 to which three transducers 9 are connected, via cables 11, to three respective ultrasound transducer connectors 7.

Each imaging system receptacle 5, labeled A, B, and C in FIG. 1, has its receptacle-to-relay signal leads 15 routed to a corresponding number of FET switches (e.g. electronic relays) 13. For convenience of illustration, only two channels are illustrated in FIG. 1, it being understood that, for a typical high resolution transducer, 256 channels are required for each transducer, i.e. 256 FET switches per transducer receptacle.

The receptacle signal leads 15 are interrupted at the respective FET switches 13 and pass through FET switches 13 only if enabled by a transducer select control line 17. Importantly, only one transducer is to be active at any one time, and therefore, only one of the control lines 17 will enable its corresponding set of FET switches 13 at any time. When a transducer is to be used, an operator must operate a switch, for example (not shown), to energize only one set of control lines 17. When the operator wishes to stop using the current transducer and use another transducer, he or she must operate the transducer select control switch (not shown) to disable the control line 17 for the transducer previously used and enable another control line 17 for engaging the connector of the newly selected transducer. The operator selector switch arrangement must be configured and wired to mutually exclusively select only one of the set of FET switches 13 for the desired transducer to be used. Upon selection of the desired transducer, the associated set of FET switches 13 are effective to connect the signal leads 15 to the relay-to-system connector leads 18 which then are routed to the electrical interface connector 19 for use by the ultrasound imaging system. The interconnections between the imaging system receptacles 5, the FET switches 13, and the electrical interface connector 19 are made by means of a printed wiring board 3.

It will be appreciated that the number of receptacles is a matter of design choice, and even in the three receptacle arrangement shown in FIG. 1, there is required 768 channels, i.e. 256 channels per transducer receptacle.

The present invention avoids the use of FET switches, and provides a means for automatically selecting the transducer in use without requiring the operator to make the selection. These and other improvements over the prior art interconnection system of FIG. 1 will become evident from the description of the remaining figures.

The invention can employ AMP interposer type contacts described in U.S. Pat. No. 5,308,252 entitled "Interposer Connector and Contact Element Therefor" by R. S. Mroczkowski et al. assigned to AMP Inc., or one of several contact methods described in U.S. Pat. No. 5,617,866 entitled "Modular Transducer System" by Vaughn Marian assigned to Acuson Corporation.

By eliminating the FET switches and making other design improvements over the prior art, the ultrasound transducer connector and multi-port imaging system receptacle assembly of the present invention is very low in manufacturing cost, is small and ergonomic, yet robust and durable. The simple basic design of the connector allows for submersion in liquid disinfectants (see U.S. patent application Ser. No. 08/538,780 or International Publication WO 97/13300, assigned to Acuson Corporation, for details of submersible ultrasound connectors). The electrical characteristics are outstanding when compared to all connectors on the market with the exception of the MP connector manufactured by AMP, Inc. for Acuson Corporation, Mountain View, Calif. The connector extension is relatively thin (less than 0.4") and, in one embodiment, is plugged into vertical receptacle slots, horizontally aligned, in the imaging system. In another embodiment, the receptacle has horizontal slots horizontally aligned.

Figure 2:
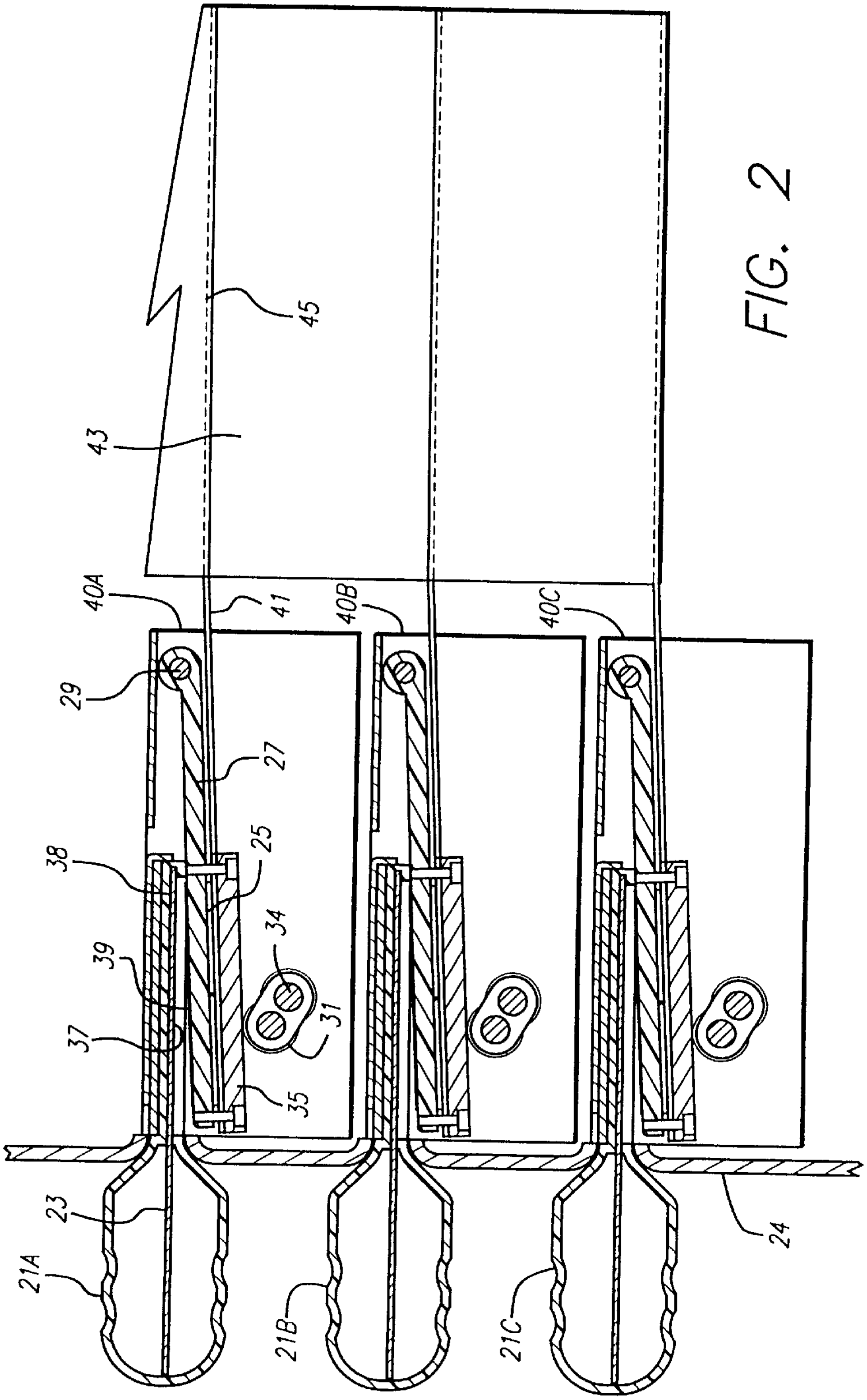
FIG. 2 is a schematic top representation of three connectors inserted into three receptacles of an ultrasound transducer connector and multiport ultrasound imaging system receptacle arrangement in accordance with the present invention.

FIG. 2 is a top view of a 3-port receptacle assembly which may be employed in a connector/receptacle arrangement in accordance with the present invention. The embodiment of FIG. 2 has three connectors 21A–C inserted in the receptacle slots, the connectors 21A–C being vertically oriented and horizontally spaced in the receptacle assembly.

In FIG. 2, all connectors 21A–21C are fully inserted into their respective receptacles 40A–C. However, none of the connectors 21A–C are electrically connected to its respective receptacle 40A–C. As will be explained hereinafter, one of the pressure rollers 31 will be rotated clockwise about its pivot axis 34, which action applies upwardly directed rolling pressure against pressure plate 35 to rotate nest plate 27 about nest plate pivot axis 29. This action moves contact nest 25 upwardly until the nest contacts 39 engage corresponding connector printed wiring board contacts 37 on one side of the connector printed wiring board 23. The contact nest 25 also makes electrical connection with the receptacle contacts (not visible) of a receptacle printed wiring board or flex circuit 41. Accordingly, when the actuation pressure plate 35 is fully closed against the connector extension 38 of one of the connectors 21A–C, all 256 contact pads 37 on the connector printed wiring board 23 engage with corresponding contact pads on the receptacle printed wiring board or flex circuit 41.

The flex circuit interconnecting scheme of FIG. 2 has the advantage of allowing additional flexibility in the placement of the individual ports. It can also be used to route the signals into a remotely located card cage (not shown) in the imaging system. This gives the industrial design great latitude in the imaging system layout.

Each receptacle 40A–40C has its printed wiring board or flex circuit 41 routed to a "Z" folded flex circuit 43, the connection being made as shown by the dashed lines at 45 in FIG. 2.

The receptacle assembly illustrated in FIG. 2 can accommodate three different connectors plugged in at any particular time. Since the connector extensions 38 are small, the width of the slots in the receptacles 40A–40C is likewise small. The receptacle is thus inherently safe, as fingers cannot access the contacts. Within the receptacle printed wiring board or flex circuit 41, contact pads (not visible) for a specific channel number are wired electrically in common for the three ports. A port which is to be selected is actuated under imaging system control by rotation of a selected pressure roller 31; only one transducer assembly can be electrically connected to the system at any one time. This considerably simplifies the imaging system by eliminating the need for electrically operated switches. In effect, a connector 21A–C and its receptacle 40A–C becomes a multi-contact relay.

Of course, with modest redesign, it is possible to accommodate even more connectors than the three illustrated, since the assembly, as noted in FIG. 2, is modular in construction. The very modest size of the connectors and the receptacle assembly allows their placement at convenient locations on the system, such as high up on the system console, beside the system monitor, or other convenient location.

Figure 3B:
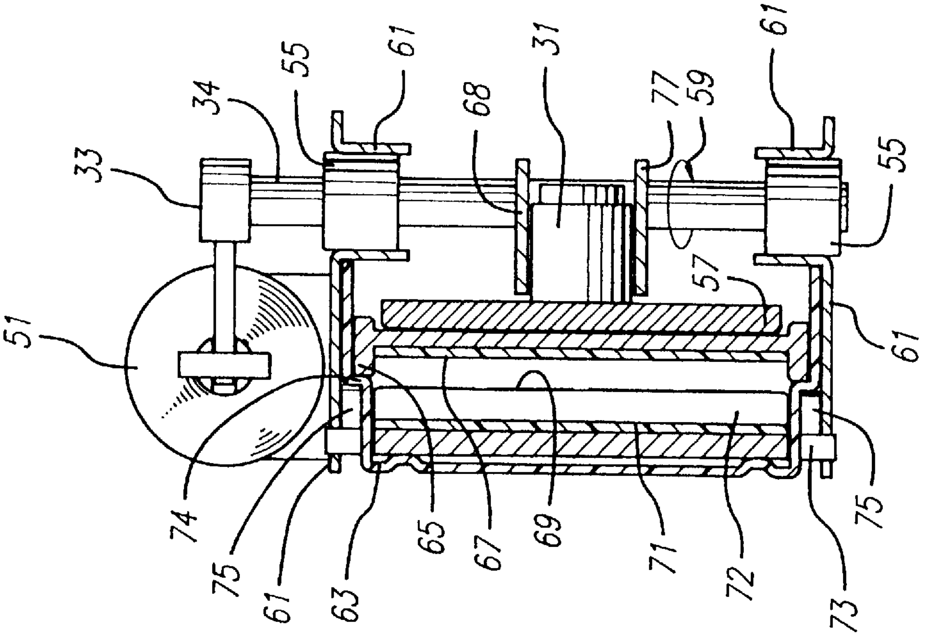
FIG. 3B is a cross-sectional view of an ultrasound receptacle assembly in the unlocked configuration in accordance with another embodiment of the invention.
Figure 3A:
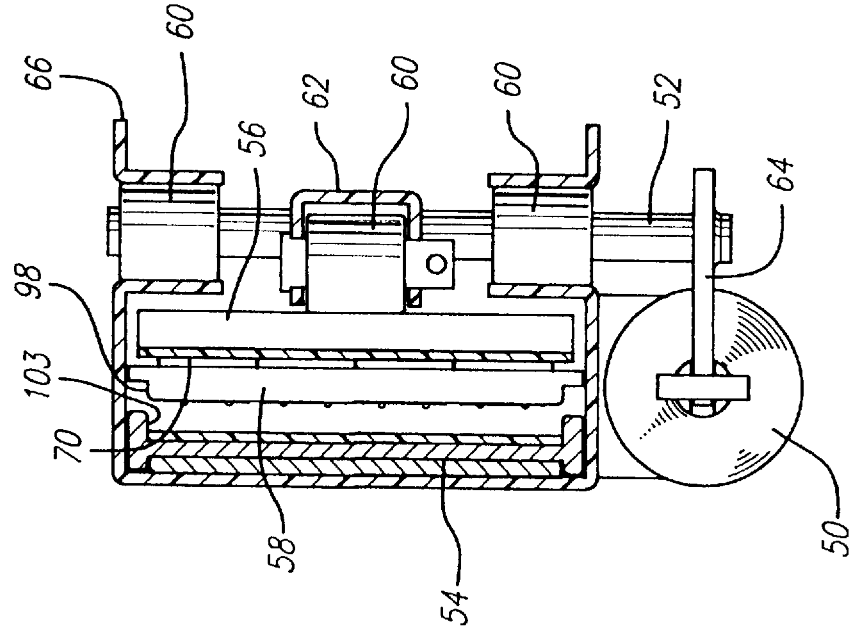
FIG. 3A is a cross-sectional view of an ultrasound receptacle assembly in the unlocked configuration in accordance with one embodiment of the invention.
Figure 7:
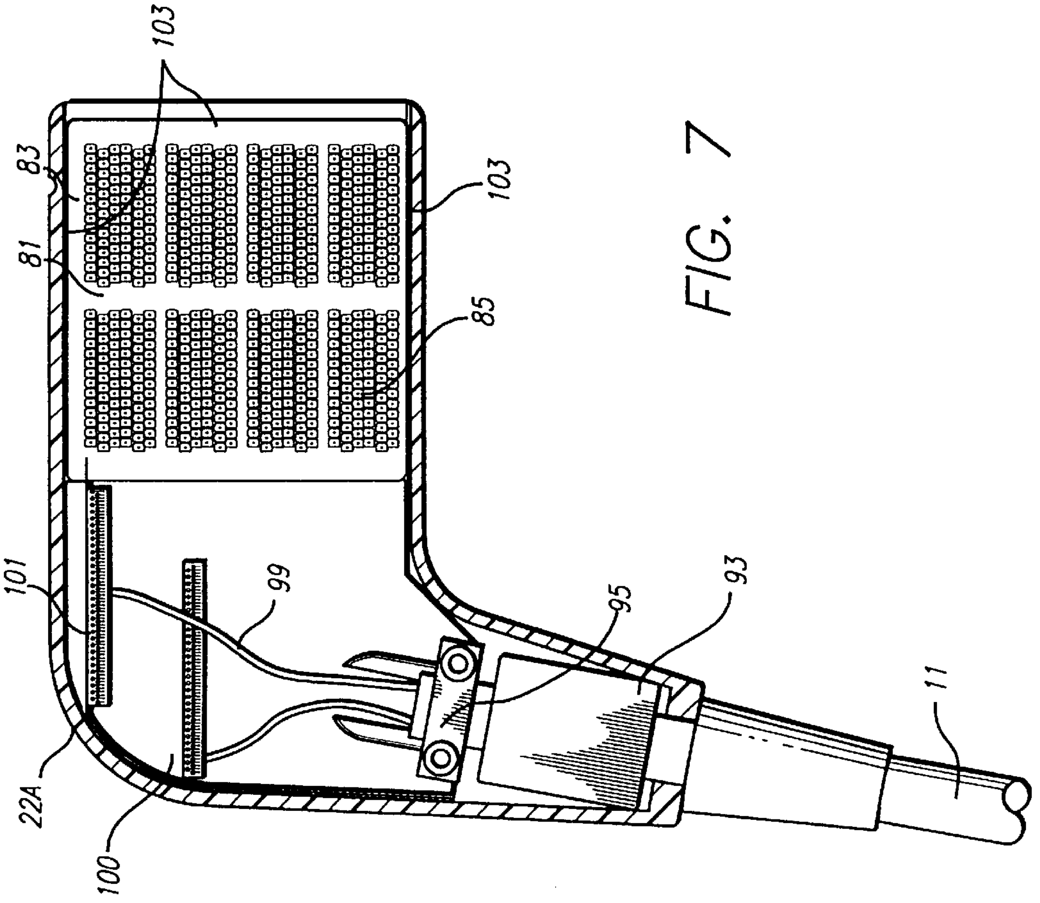
FIG. 7 is a view similar to that of FIG. 4, but with the cover removed to show the connection of the multi-coaxial conductor cable to the connector pads.
Figure 6:
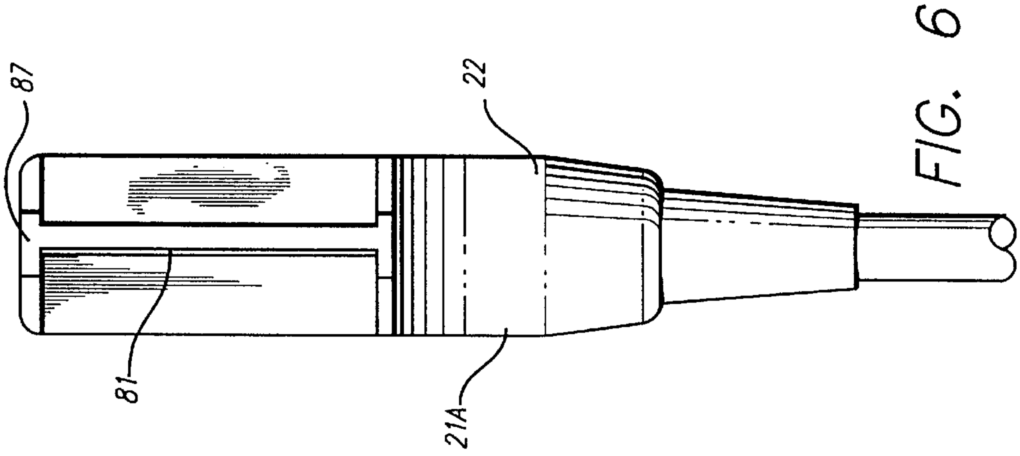
FIG. 6 is a front view of the connector of FIG. 4.

Two embodiments of compatible receptacle assemblies are shown in FIGS. 3A and 3B in partial cross-sectional representation. Details of a compatible connector 21A is shown in FIGS. 5–7.

From these figures, it will be observed that the connector 21A has 16 contact pad groups 85, each having 28 contact pads thereon, making a total of 448 contact pads, which is quite adequate for a 256 channel ultrasound transducer as well as peripheral devices such as motor drive, position sensors, etc. The contact pads 85 are on a multi-layer, e.g. 8 layer, printed wiring board 81 which also includes coaxial conductor termination pads 101. The contact pads 85 are hard gold plated in the same manner as those on the MP connector found on the Sequoia™ultrasound imaging system manufactured by Acuson Corporation, Mountain View, Calif. The OEM supplier is AMP, Inc. of Harrisburg, Pa. Other plating systems may be required for greater life expectancies (up to 100,000 cycles). The coaxial conductor termination pads 101 are located on both sides of the connector printed wiring board 81; they can accommodate coaxial conductors 99 as large as 38 gauge.

The coaxial conductors 99 comprise the flexible cable 11 between the transducer connector and the transducer itself, the cable 11 being restrained by a cable clamp 95 in a known manner. Also incorporated into the design of the connector 21A is a ferrite isolator for rf noise immunity. The housing 22 includes two injection molded plastic parts one of which, 22A, is shown in FIG. 7, the other part (not shown) removed to show the coaxial conductor termination scheme.

The plastic housing 22 has a retention detent 83 which is engaged by the imaging system receptacle 40A–40C. This feature assures that the connector extension 87 is properly located within the receptacle 40A–C for proper actuation to be accomplished, even before contact engagement is made. The “window”, i.e. raised frame, 103 around the array of contact pads 85 is designed to properly locate the pads 85 with respect to the contacts 39 in the receptacle 40A–C during actuation. This “window” technique reduces the tolerance required in the other parts of the connector/receptacle arrangement, reducing costs and increasing reliability.

In the embodiment of the connector/receptacle assembly of FIG. 2, a contact nest 25 is shown and was described as the element which electrically connects the connector contacts to the receptacle contacts. In such an embodiment of the receptacle assembly, and in other receptacle embodiments in this specification, reference is made to U.S. Pat. Nos. 5,308,252 and 5,358,411. While these references teach the use of contact springs which make a wiping action across the corresponding contact pads on either side thereof, thereby establishing a reliable electrical connection between the contact pads on either side, other means of contacting the connector contacts 37 with the receptacle contacts 39 may be employed in the present invention. That is, the invention is not limited to the use of a contact nest 25 as shown and described herein.

FIG. 3A is a partial cross-sectional view of one port of the receptacle assembly illustrated in FIG. 2. In this embodiment, a linear actuator 50 reciprocates the end of an actuation crank 64 (in and out of the paper as shown in FIG. 3A), which, in turn, rotates actuator shaft 52. Shaft 52 is rotatably supported by the outer two roller bearings 60 fixed relative to a framework 66. The middle roller bearing 60 has its axis parallel to the axis of shaft 52, the axis of the middle bearing 60 being movable along a circular path spaced from the axis of shaft 52. As shaft 52 rotates, the middle roller bearing 60 is articulated in the left-right directions as viewed in FIG. 3A which, in turn, applies pressure against actuation plate 56 upon which is mounted the nest plate 58. Movement of nest plate 58 toward the connector extension 54 serves to electrically connect the contacts on connector extension 54 with the nest contacts on nest plate 58. Rotation of shaft 52 in the opposite direction withdraws the nest plate 58 away from connector extension 54 permitting the connector extension 54 to be removed from the receptacle slot.

The flat actuation plate 56 is engaged by the middle roller bearing 60 to distribute force over the entire back side of the receptacle printed wiring board 70 during actuation. The nest plate 58 and actuation plate 56 form a sandwich, with the contacts and the printed wiring board, or alternative flexible circuit, 70 in between.

As described, the linear actuator 50 converts linear motion from the actuator (which may employ pneumatic, hydraulic, solenoid, screw/motor, or other movement actuation means) to rotary motion of the shaft 52. This causes the actuation plate 56 and nest plate 58 assembly to displace toward the connector extension 54 causing the receptacle contacts to make contact with the contact pads on the connector extension.

The frame 66 ties the components together and supplies the reaction force required to compress the contacts into the pads on the connector extension 54.

The nest plate 58 and actuation plate 56 assembly moves in an arc about a pivot point with respect to the frame 66, in a manner as shown in the arrangement of FIG. 2.

In this connection, as also can be viewed in FIG. 2, the imaging system front panel 24 is a molded plastic bezel which funnels the connector extension 38 of a connector 21A–C into the vertically oriented ports of the receptacle assembly.

FIG. 3B shows an alternative construction for a receptacle assembly. In FIG. 3A, the actuator member 62 presses the nest plate 58 into contact with the connector extension 54. In FIG. 3B, the connector extension 65 is moved by load plate 57 into contact with the contact nests of the receptacle.

The linear motion of the linear actuator 51 is converted to a rotational motion 59 through actuator shaft coupler 33 in a manner similar to that described in connection with FIG. 3A. Actuator shaft 34 is supported by roller bearings 55 which in turn rotates actuator member 68 moving pressure roller bearing 31 into pressing engagement with load plate 57.

Connector extension 65 is biased away from the contact nests 69 of the receptacle by means of a pair of compression springs 75 which may be in the form of leaf springs or coiled compression springs. When pressure roller bearing 31 moves load plate 57 against the connector extension 65, the top and bottom edges of connector extension 65 press against the shoulder 74 of a moving frame 63 against the bias of springs 75 and collapses springs 75 to bring the connector printed wiring board 67 of connector extension 65 into contact with the contact nests 69 of the receptacle. A receptacle printed wiring board or flex circuit 71 carries signals from the contact nests 69 to the ultrasound imaging system electronics. Thus, in the embodiment of FIG. 3B, although the connector extension 65 is translated by the actuator 51, the receptacle printed wiring board or flex circuit 71, the nest plate 72, and contact nests 69 remain stationary in the receptacle, being fixed in place by bolster plate 73 attached at both of its ends to the receptacle frame 61.

FIGS. 4–7 show one example of an appropriate connector 21A which may be adapted to fit into the receptacles shown and described in FIGS. 2, 3A, and 3B. Many other forms of the connector are envisioned, and the particular designs shown in FIGS. 4–7 are to be treated as exemplary only.

The connector 21A of this embodiment includes a housing 22 the rear end of which serves as a hand grip, the forward end being narrowed to define the connector extension 87. A retention detent 83 is formed on the top of the connector and cooperates with a resiliently biased bar or dog (not shown) in the system receptacle. When a connector 21A is inserted into a system receptacle, this features assures that the connector extension is properly located and retained within the receptacle for proper actuation to be accomplished, i.e. for appropriate registration of the contact pads 85 on connector printed wiring board 81 with the corresponding pads of the contact nests 69 of the receptacle (the FIG. 3B as an example).

The contact pads 85 are arranged in groups of 28, there being 16 contact pad groups on the connector printed wiring board 81, as shown. The 448 contact pads are sufficient in number to permit 256 channel ultrasound transducer operation, including contact pads to route signals for peripheral devices such as motor drives, position sensors, etc.

The connector printed wiring board 81 is preferably an eight layer printed wiring board which also includes coaxial conductor etermination pads 101. The termination pads 101 are connected to respective contact pads 85 through the multilayer printed wiring board 81. The multi-coaxial conductor cable 11 from the transducer enters the housing 22 and passes through a ferrite isolator 93 providing rf noise immunity. The cable 11 then is passed through a securing cable clamp 95 for strain relief and cable attachment to the housing 22. After passing through cable clamp 95, the outer insulation and ground shield layers (not shown) are stripped away leaving individual coaxial conductors 99 to follow an appropriate layout pattern for connection to the coaxial conductor termination pads 101. The center conductor of each coaxial conductor 99 is thus connected to an assigned contact pad 85, and the ground shield of each coaxial conductor (not shown) may be soldered to a ground plane 100. The shield solder connections and center conductor solder connections for each coaxial conductor are not shown in the drawing, as these are commonly understood construction details for ultrasound transducer connectors.

To assist in proper alignment of the contact pads 85 with the corresponding contact nests of the receptacle, a window frame 103 around the contact pads 85 is provided. A complementary interengaging window frame (actually a rabbet 98 around the edge of the contact nest plate 58, such as that shown in FIG. 3A) is provided within the receptacle arrangement, so that when the connector extension 87 is brought into contact with the contact nests of the receptacle, the making of the conductor and receptacle window frames automatically align the contact pads for proper registration.

FIG. 8 is a representation in partial cross-section of an alternate embodiment of an ultrasound transducer connector 111 having a connector printed wiring board 114 within housing 115 having a housing extension 115A. A connector extension locking lug 119 and the end 119A of the extension 119 establish a reference (left to right) for the connector when it is mated in the receptacle described below with reference to FIGS. 9 and 10. Correct alignment of the contact pads in the connector 111 with corresponding pads within the receptacle 121 is required for proper functioning of the connector/receptacle system. Single or multiple openings 117 molded into the housing extension 115A provide mechanical and electrical access to contact pads on the back side of the printed wiring board 114. The shape of opening 117 together with the mechanical design of the mating components in the receptacle 121 (described below) serve the same purpose as the retention detent 83 described in connection with FIGS. 4–7; the connector is assured to be correctly located within the receptacle 121 before electrical engagement of the signal contacts between the connector printed wiring board 114 and the contact nest 127 of the receptacle 121 has been effected.

As may be appreciated by reference to the drawing of FIGS. 8 and 9, as the rounded blunt nose of the connector extension 115A enters receptacle slot 123, the conductive detent roller 131 is pushed slightly downwardly to pivot about nest plate pivot 125A, such pivoting action being slightly resisted by the spring plunger assembly 141 applying a resilient force against the "L" bracket detent frame 145 by plunger 142. After the distal end of housing extension 115A passes by the axis of conductive detent roller 131, roller 131 is permitted to return upwardly to engage the ground plane 113 of connector 111 due to the detent roller 131 moving into opening 117 on the side of connector 111 opposite the connector extension hook 119. As a result of this action, the connector extension locking lug 119 engages corresponding features (not visible in FIGS. 9 and 10—to be detailed with reference to FIGS. 11 and 12 which follows) on the sides of the contact nest plate 125 so as to properly locate (left and right directions) the contact pads on printed wiring board 114 to contacts within the contact nest 127.

In the condition in which the connector and receptacle signal contacts are not engaged, if an operator wishes to pull the connector 111 out of engagement with the receptacle 121, a moderate pulling force will bias conductive detent roller 131 downwardly due to the sloping edges of opening 117 in the connector 111 to accommodate the withdrawal.

After insertion of the connector 111 into receptacle slot 123, conductive detent roller 131, as mentioned, electrically contacts the ground plane 113 of the connector 111 through opening 117. This is an important feature of the invention, in that, although the electrical imaging contact pads have not yet been mutually engaged between connector and receptacle, a ground connection (and other connections, as desired) is made between these two members to enable automatic detection by the ultrasound imaging system as to which transducer is being used. Details of this feature of the invention will be described hereinafter.

In FIGS. 9 and 10, it will be observed that a "transducer-in-use" spade lug connector 137 is electrically coupled to the conductive detent roller 131, the roller 131 assembly being mounted on "L" bracket detent frame 145 by means of a screw 137. An insulator 133 electrically isolates the spade lug connector 137 with respect to the detent frame 145.

The nest plate 125 supports the contact nest 127 and pivots about nest plate pivot 125A when an actuator shaft 129 is operated to pivot the nest plate 125 downwardly from the position shown in FIG. 9 to the position shown in FIG. 10, the latter demonstrating a full engagement of the connector 111 in the receptacle 121 with the contact pads of the connector printed wiring board 114 being in registration contact with the contact nest 127.

In the reverse operation, the release of connector 111 is effected by movement of actuator shaft 129 upwardly, acting against the return frame 146 to pivot nest plate 125 upwardly about nest plate pivot 125A, i.e. returning the nest plate 125 to the FIG. 9 position.

Microswitch 139 detects the presence of a connector in the receptacle in the clamped condition. That is, when the nest plate 125 is in the position shown in FIG. 10, "L" bracket detent frame 145 is pivoted about nest plate pivot 128 sufficiently to actuate the plunger on microswitch 139, and spade lugs 147 conveys this sensed information to the system via the flex circuit 153. In FIGS. 9 and 10, the dotted lines encompassing "Transducer-in-use" spade lug connector 137 and microswitch spade lugs 147 indicate that the electrical connections to these spade lugs are made to the flex circuit 153 in an appropriate and known manner.

Figure 11:
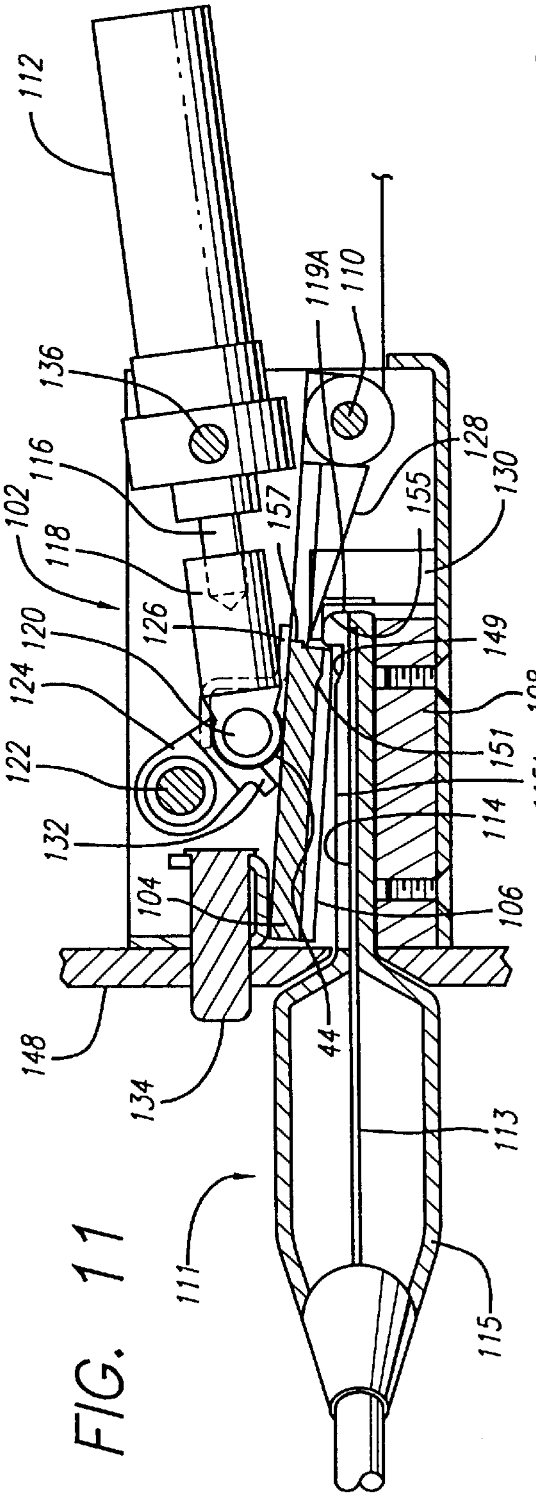
FIG. 11 is a partial cross-sectional view of yet another embodiment of a connector and receptacle assembly in accordance with the present invention with the connector inserted into the receptacle in an unlocked condition.
Figure 12:
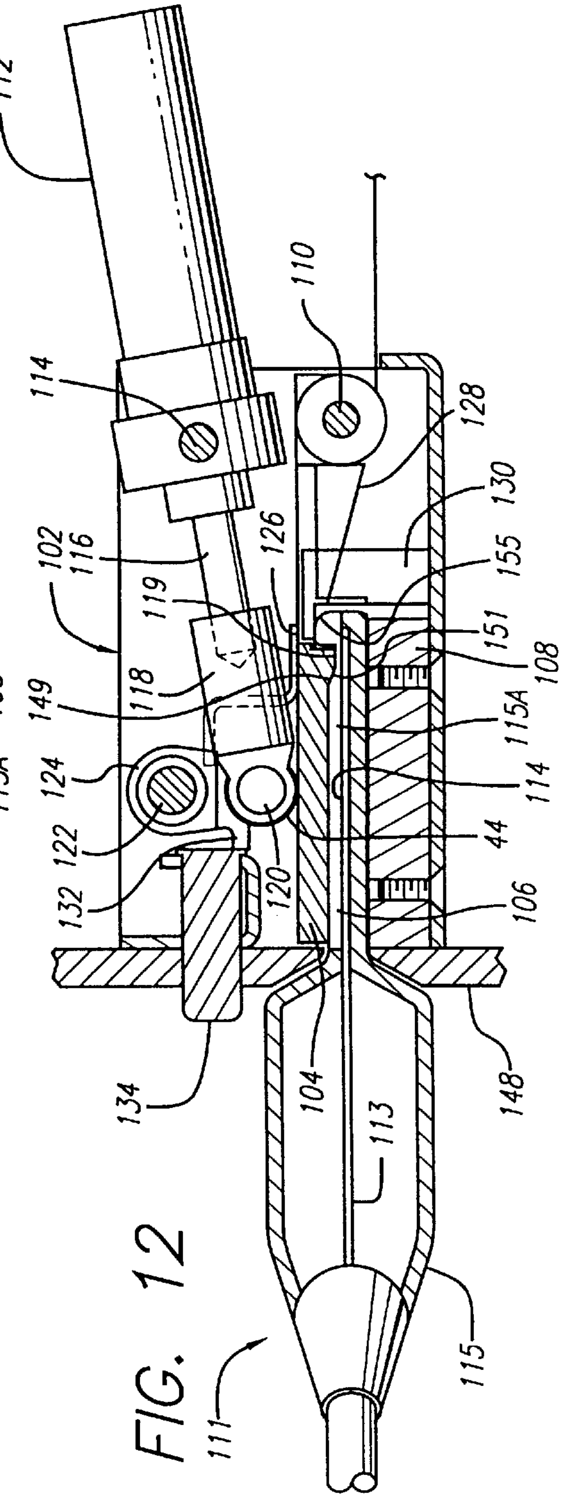
FIG. 12 is a view similar to that of FIG. 11, but with the receptacle in a locked condition electrically connecting the connector with the receptacle.

FIGS. 11 and 12 show yet another, and preferred, embodiment of a receptacle compatible with the design of the transducer connector 111 shown in FIG. 8. In FIGS. 11 and 12, the portion of the connector housing 111 having an opening 117 (FIG. 8), and the conductive detent roller 131 (FIG. 9) are not shown for convenience, as these elements operate in the same manner as was described in connection with FIGS. 8–10. The details of FIGS. 11 and 12 are thus offered to show an alternative connector clamping scheme.

In this connection, FIGS. 11 and 12 show the locating features described broadly with reference to FIGS. 8 and 9. When connector 111 is initially inserted into a receptacle 102, it is pushed forward until the nose of extension 115A abuts stop bracket 155 which limits the insertion depth. In this position, the signal contact pads on the connector printed wiring board 114 are spaced from the contacts of the contact nest 106. As contact next 106 is pivoted downwardly by actuator 112, the sloping distal edge 157 of the contact nest plate 104 slides against and pushes the connector extension locking lug 119 toward the insertion direction, while the sloping edge 151 of the contact next plate 104 continues to move downwardly until it is seated against the sloping wall 149 of the connector extension 115A. This causes a wedging effect in which the forward most end on each side of the contact nest plate 104 precisely fits into a complementary shaped cutout defined by locking lug 119 and sloping wall 149. This is best observed in FIG. 12 where it is clear that such wedging effect aligns the connector 111 and receptacle 102 longitudinally in the insertion direction. Interengaging window frames guide and maintain the connector 111 and receptacle 102 laterally of the insertion direction in the manner described with reference to FIGS. 3A and 7.

In FIG. 11, an air cylinder actuator 112 is mounted to the receptacle 102 by means of an air cylinder pivot axle 136. The plunger 116 moves in and out of air cylinder actuator 112 under ultrasound system control. In turn, the distal end of plunger 116 is fixed to a roller yoke 118 pivotally coupled to a roller axle 120. obviously, other types of actuators, or a manually actuated lever, could be used in place of the air cylinder actuator 112 shown. Examples are a hydraulic cylinder, a solenoid, lead screw and motor arrangement, etc.

The roller axle 120 has a roller 44 journaled thereon to roll against the top surface of nest plate 104. Alternatively, with the proper choice of materials for the top of nest plate 104 and the end of roller yoke 118, a roller may be eliminated, and the rounded distal end of roller yoke 118 may apply a low-friction sliding pressure against the top of nest plate 104 to rotate nest plate 104 about nest plate pivot 110 in order to engage the contact nest 106 of the receptacle with the connector printed wiring board 114 of the connector 111.

When the plunger 116 is fully extended from the air cylinder actuator 112, the roller link 124 has rotated clockwise until release trigger 132 engages and is stopped by the manual ejection button 134. In this configuration, the roller link 124 has rotated slightly over center with respect to roller link pivot axis 122 and roller axis 120. Thus, when the air is removed from the air cylinder actuator 112, the nest plate 104 remains clamped.

The fully clamped condition as just described is shown in FIG. 12. In the clamped condition, the contact nest 106 are connected to the system via a flex circuit 128. When the transducer associated with transducer connector 111 is not in use, the receptacle 102 must return to its unclamped condition. To do so, the system detects the non-use of the transducer involved and pulls back on plunger 116 from the FIG. 12 position to the FIG. 11 position. In doing so, the roller 44 is pulled back against the "Z" shaped extractor 126 which pulls the nest plate 104 upwardly to pivot about nest plate pivot 110 and return to the FIG. 11 condition. The extractor 126 forces the nest plate 104 to follow the roller link 124 when disengaging. Also, when disengaging, the connector extension retainer 130 keeps the connector 111 from following nest plate 104. After return of the nest plate 104 to the FIG. 11 position, the connector 111 may be removed from the receptacle 102 as hereinbefore described in connection with FIGS. 8–10.

In the event of a malfunction of the air cylinder actuator 112, or for any other reason, a manual ejection button 134 is provided. With reference to FIG. 12, the roller link 124, pivotable about roller link pivot axis 122, is provided with a release trigger 132 extending toward the system front panel 148. When manual ejection button 134 is pressed into the panel 148, it engages release trigger 132 and forces roller link 124 to pivot counterclockwise and move roller yoke 118 rearwardly, releasing the pressure against nest plate 104 and allowing it to be pivoted back to its unclamped condition shown in FIG. 11 for easy removal of connector 111 from receptacle 102.

Figure 13:
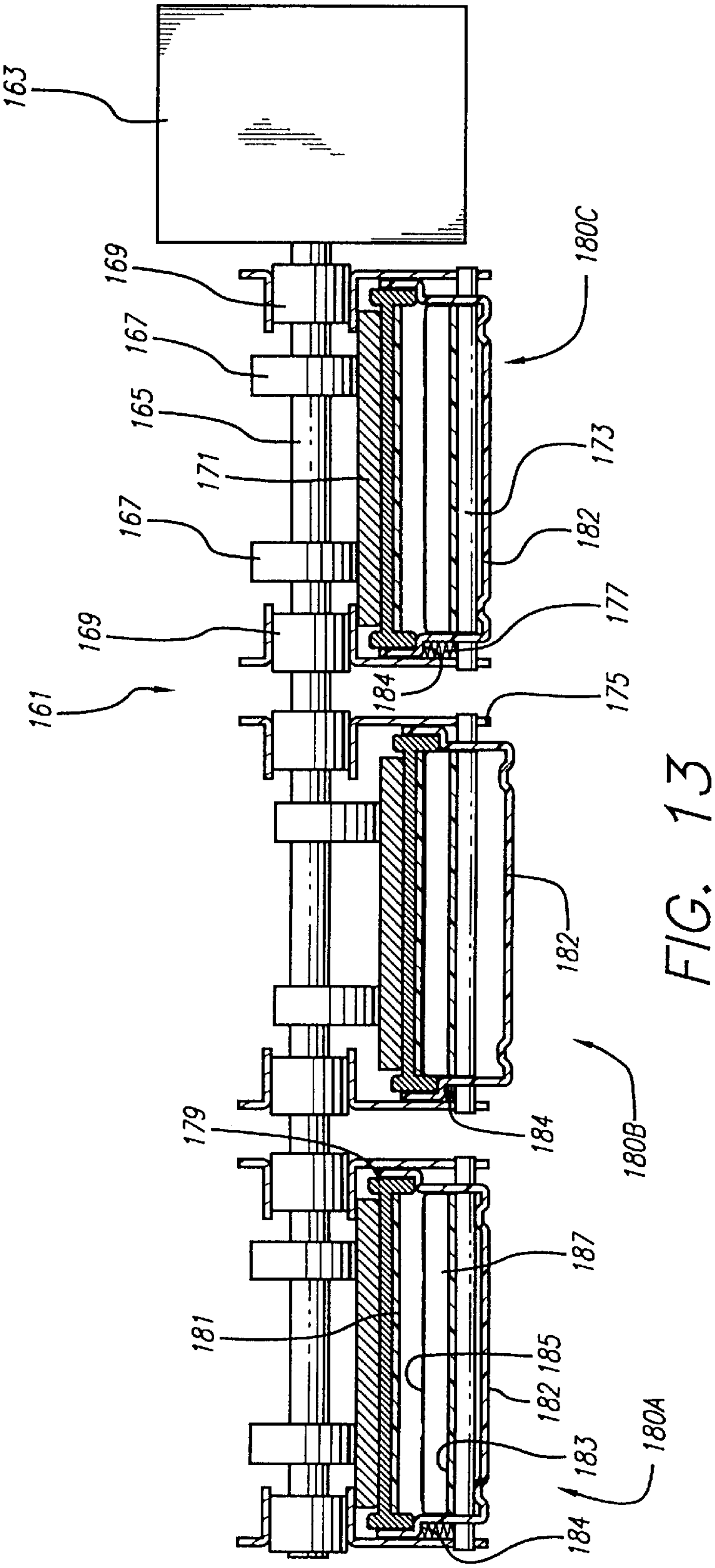
FIG. 13 is a partial cross-sectional view of three receptacles horizontally arranged for receiving three ultrasound transducer connectors, and with a power unit driving a common shaft for mutually exclusively locking one of the receptacles to its inserted connector.

An alternative layout for the three receptacle ports is illustrated in FIG. 13. In this arrangement, the ports are oriented in a horizontal manner and horizontally spaced, so that all three mechanisms are serviced by one shaft 165. This arrangement has several advantages which include only a single rotary actuator 163, which may be implemented by a geared, or stepper, motor 163 for all three ports. Each port has a pair of bearings (e.g., Torrington bearings) 169 within which the common shaft 165 rotates. Each port is also provided with a pair of cams 167 fixed to shaft 165 and spaced angularly 120 degrees. This ensures that only one connector is engaged by its respective receptacle at any time. As with the previously described port arrangement, the imaging system provides the proper drive signal to the actuator 163 responsive to either a manually selected transducer selection or automatically by the operator picking up a transducer to be used.

In FIG. 13, the horizontally oriented multiport receptacle assembly 161 is provided with three identical receptacles 180A, B, and C. Each receptacle 180A–C is configured the same as that shown and described in connection with FIG. 3B. That is, each receptacle 180A–C has a moving pressure platen 171 movable by the cams 167 for applying a pressure against the connector extension 179 having a connector printed wiring board 181 on one side surface facing a contact nest 185 of a nest plate 187. The nest plate 187 makes multiple contact with the registered contact pads of a system printed wiring board 183. When the cam 167 of a particular receptacle 180A–C is moved to the unclamped rotational position, a pair of leaf or coil compression springs 177 presses against a horizontal offset shoulder 184 to return the moving frame 182 to an open condition, and this, in turn, moves the connector extension 179 and moving pressure platen 171 away from the contact nest 185 in order that the connector extension 179 may be removed from the receptacle 180A–C.

As noted above, since the cams 167 for three ports are oriented 120 degrees apart on the shaft 165, only one port can be actuated at any particular time. Thus, the required exclusivity is implemented mechanically in the receptacle assembly instead of electronically in the imaging system controller. The cost of such an arrangement will thus be typically lower than the vertical configuration shown in FIG. 2. However, the flexibility of this arrangement for the industrial designer is somewhat reduced.

Figure 14:
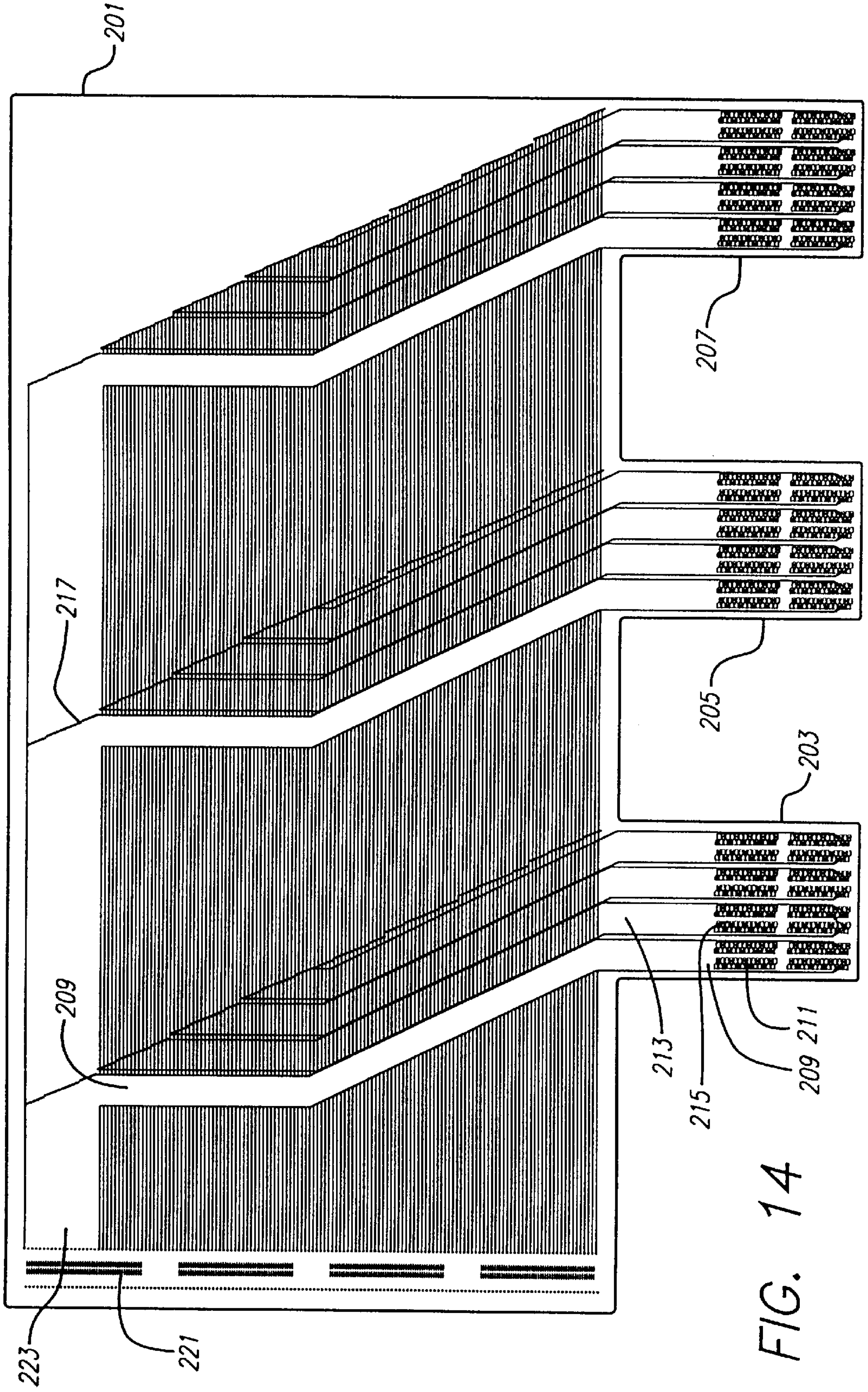
FIG. 14 shows a receptacle printed wiring board in which three receptacle printed wiring board contact pads are connected in parallel by a plurality of connector routing traces on the printed wiring board leading to a system connector.

A conceptual design for a receptacle flex circuit 201 is illustrated in FIG. 14. Flex circuit 201 is a four layer Kapton (Trademark of DuPont, Inc.) based flexible circuit which electrically interconnects the contact pads 211 of a receptacle printed wiring board contact pad extension 203 to system connectors 221 which are interfaced to mating receptacles in the imaging system chassis (not shown). The contact pads 211 connect to a trace group 209. The traces of trace group 209 make electrical connection to corresponding ones of the traces of connector routing traces 223. Connections between layers and between the trace groups and routing traces of flex circuit 201 are accomplished by standard plated through vias.

The schematic diagram of FIG. 15 is one example of a "transducer-in-use" detecting system which has been described generally herein to this point. FIG. 16 shows signal waveforms and the timing thereof for the circuit of FIG. 15.

A 50 KHz oscillator 301 provides an rf signal source for the "transducer-in-use" detecting system. For example, the signal from oscillator 301 may be about 12 volts peak-to-peak and sinusoidal. This rf signal at point A of the schematic of FIG. 15 is rectified by diode 337 and filtered by the RC network 339, 341. The time constant of the RC network 339, 341 is great as compared to the frequency of the rf signal source 301, and thus the negative input of comparator 343 has a DC reference voltage as one of its inputs.

The rf signal at point A is also conveyed to the transducer 9 through a contact roller 303 within the receptacle (not shown), making contact with sense signal injection line 305. Injection line 305 is the center conductor of a coaxial conductor 99 leading to the transducer 9 and is electrically coupled there to a sense signal electrode (e.g., plate) 307. A second, detection line electrode (e.g., plate) 315 lies adjacent the sense signal electrode 307, such that when an operator 311 picks up the transducer 9 for usage, the operator 311 provides a capacitive coupling between the two electrodes.

That is, a capacitive coupling 309 exists between the operator 311 and sense signal electrode 307, and also a capacitive coupling 313 exists between the operator 311 and the detection line electrode 315. Thus, when the operator picks up the transducer 9 for usage, a capacitive coupling path between the two coaxial conductors 99 in the cable assembly 11 exists, and due to the high frequency of the rf signal source 301, the small capacitance that the operator 311 possesses with respect to the electrodes 307 and 315 produces a "transducer-in-use" detection signal on the detection line 317 which is electrically in contact with contact roller 319. The signal on contact roller 319 is developed across resistor 325 and is shown in the timing diagram of FIG. 16 as waveform C. Waveform C is amplified by amplifier 327 which has a gain control 329 that the operator may adjust to set the threshold for the comparator 343 (to be described later).

The output of amplifier 327 passes through diode 331 to be rectified and filtered by the RC network of resister 333 and capacitor 335 to produce signal B as shown in FIG. 16. Although signal C is somewhat less in amplitude than signal A due to losses and capacitive coupling to ground, the amplitude of the signal from amplifier 327 is greater than signal A, so that, when rectified, the DC voltage at point D is greater than the DC voltage at point B. Since the signal at D is applied to the positive terminal of comparator 343, and since the comparator 343 is an inverting circuit, when the DC signal level at point D is greater than that at point B, the output E of comparator 343 goes to a low level. This occurs when the operator 311 holds transducer 9 to provide the capacitive coupling 309, 313.

When the operator 311 releases the transducer 9, and capacitive couplings 309, 313 no longer exist, the voltage on detection line 317 drops significantly. The input to amplifier 327 is thus a small 50 KHz signal which, when rectified at point D is less than that of the DC level at point B. In such a case, the negative input to comparator 343 is greater than that on the positive input, and the inverting comparator provides a high level output, typically 5 volts at point E. Thus, as FIG. 16 indicates, when the operator 311 is not touching transducer 9, the output at E is at about 5 volts, and when the operator is holding the transducer 9, the output E from comparator 343 is approximately 0.7 volts.

The schematic diagram of FIG. 15 and waveform chart of FIG. 16 represents only a single detection scheme for indicating to the imaging system that a particular transducer is being used. A number of other schemes may be used instead. For example, a simplified "transducer-in-use" detection scheme may only detect the difference in noise picked up on a ground line in the transducer cable 11 when the operator is holding a transducer and when he or she is not holding the transducer. When held, there would be a larger level of noise picked up on the ground line, and this increase could be detected to produce a "transducer-inuse" signal.

Figure 17:
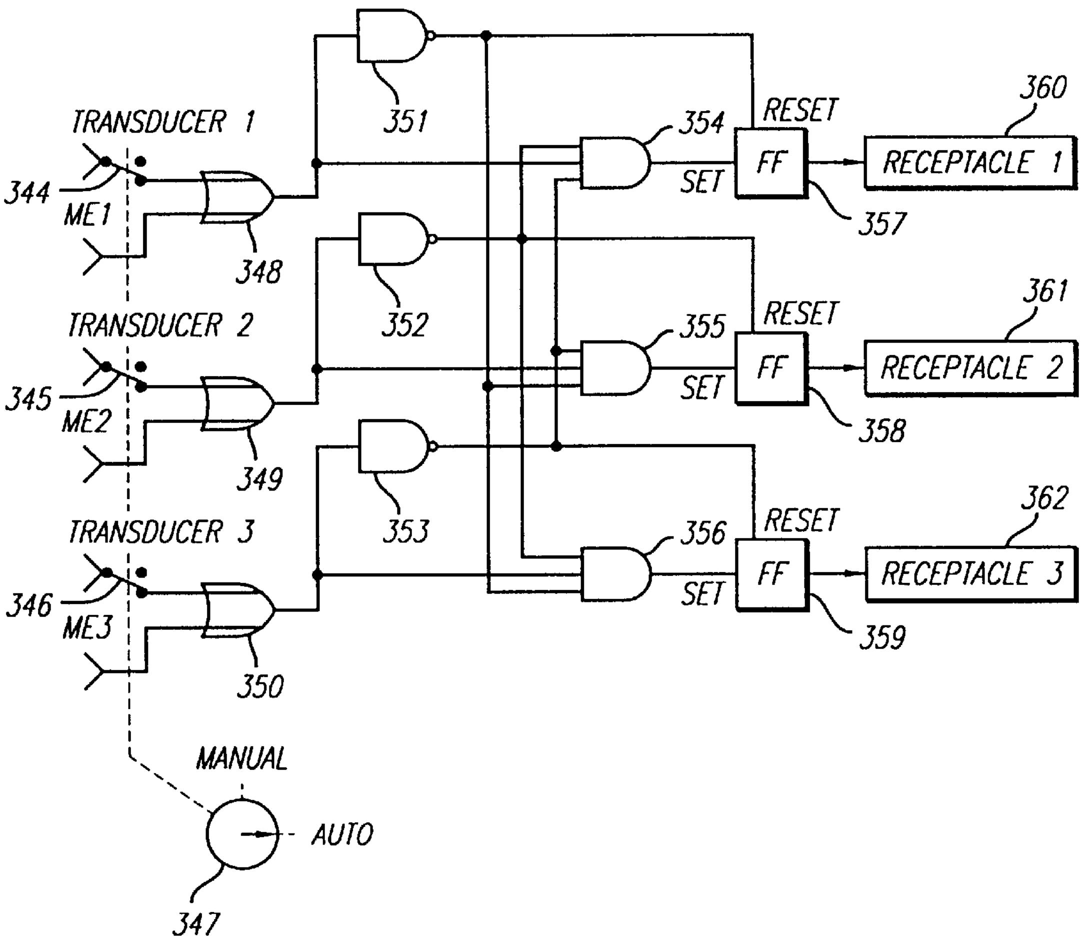
FIG. 17 is a block diagram of a priority selection circuit to insure that two transducers are not clamped in the receptacle assembly at the same time.

FIG. 17 is a simple logic circuit arrangement designed to eliminate the possibility of two receptacles being clamped and in operating engagement with their respective connectors. As mentioned, it is essential for only one receptacle to be clamped at any one time. The circuit of FIG. 15 will meet this requirement for so long as the operator (or different operators/personnel) does not pick up and hold two transducers at the same time. The circuit of FIG. 17 gives priority to the first transducer picked up, and will retain priority for that transducer even if another transducer is subsequently picked up before the first transducer is released.

Assume transducer 1 is picked up in FIG. 17. The touching by the operator produces a positive level "transducer-in-use" signal as seen in FIG. 16. This high level is sent as one input to AND gate 354 and is also inverted by inverter 351 and applied to the reset input of flip-flop 357 as well as to the inputs to AND gates 355 and 356 related to transducers 2 and 3.

Flip-flop 357 can only be set by all three inputs to AND gate 354 going positive. This can only happen if transducer 1 is touched and transducers 2 and 3 are not being touched. Thus, exclusively, if transducer 1 is touched and transducers 2 and 3 are not touched, flip-flop 357 is set, and its output is sent to receptacle 360 to clamp the inserted connector of transducer 1 in receptacle 1.

Note that when the conditions of the preceding paragraph are met, the inputs to AND gates 355 and 356 necessarily are low, preventing flip-flops 358 and 359 from setting and clamping receptacles 2 and 3. Also, necessarily, with transducers 2 and 3 not being touched, the outputs of inverters 352 and 353 are high, resetting flip-flops 358 and 359.

In the event that another transducer, e.g. transducer 2 is touched, the middle input of AND gate 355 goes high, but the lower input to gate 355 is low due to transducer 1 being previously touched. Therefore, even though flip-flop 358 is no longer being reset, it cannot be set until transducer 1 is released. At that time, all three inputs to AND gate 355 are high; flip-flop 357 is reset via inverter 351; and flip-flop 358 is set by the output of AND gate 355.

The same analysis applies to other conditions of touching and non-touching of the three transducers. Importantly, in order for any receptacle 360, 361, or 362 to be clamped, it requires that the transducer connected to the connector inserted in it must be touched and the other two transducers not touched.

If the transducer-in-use detection system is used, transducer selection is automatic, as described. However, operation of the receptacles may be optionally under the control of the imaging system. A particular transducer can be selected by the operator manually, providing an input to the control panel of the imaging system. To implement this function, OR logic gates 348–350 and a manual/automatic switch 347 are provided. Switch 347 has three sets of single-pole double-throw switch contact sets 344–346 which, when switch 347 is in the manual position, disconnects the transducer-in-use signals from all three OR gates 348–350. In order to get any one transducer connector to be engaged with the receptacle into which it is inserted, any one of the manual enable inputs, ME1–ME3, are brought to a high logic level (e.g., +5 volts), and this replaces the automatic +5 volt enabling signal from the transducer-in-use circuit of FIG. 15. Whether the inputs to OR gates 348–350 are from the transducer-in-use circuits or are manually applied, the feature of not permitting more than one transducer connector to be engaged is equally effective. If desired, simple additional switching circuitry can be employed to select only automatic operation or manual operation. Using the circuit of FIG. 17, any transducer may be manually activated by bringing a selected one of inputs ME1–ME3 high independent of whether switch 347 is in the automatic or manual mode. In such a case, only the automatic selection may be disabled; the manual selection remains available at any time. This may be advantageous in certain situations.

FIGS. 18–40 depict variations on the design of the connectors and/or receptacles, using the basic and general concepts described in connection with FIGS. 1–17 and the corresponding text in this specification.

Figure 18:
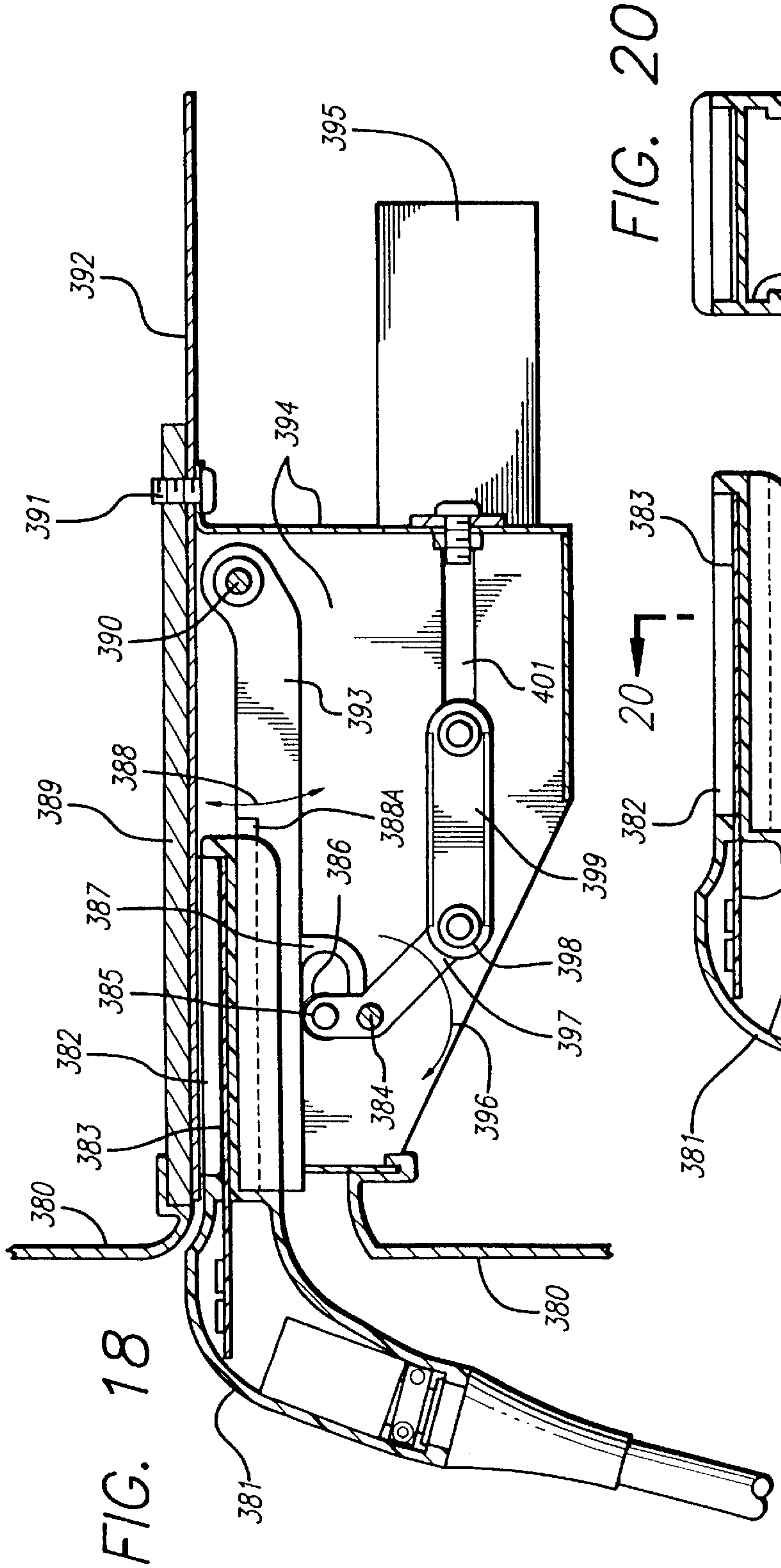
FIG. 18 is a partial cross-sectional view of an alternative connector and receptacle arrangement in a clamped condition.

In FIGS. 18–21, a connector 381 is inserted into a horizontal slot in front panel 380, connector 381 exposing the contact pads 383 of a connector printed wiring board 402. The receptacle in FIG. 18 is in the locked, or clamped, condition in which the receptacle nest plate 382 has exposed contact nests 406 facing downwardly, each contact nest having typically 408 contacts (12 groups of 34 contacts each). A rigid aluminum bolster 389 is fixed to the frame 394 and front panel 380 and supports the receptacle printed wiring board 392 in a fixed position.

Figure 21:
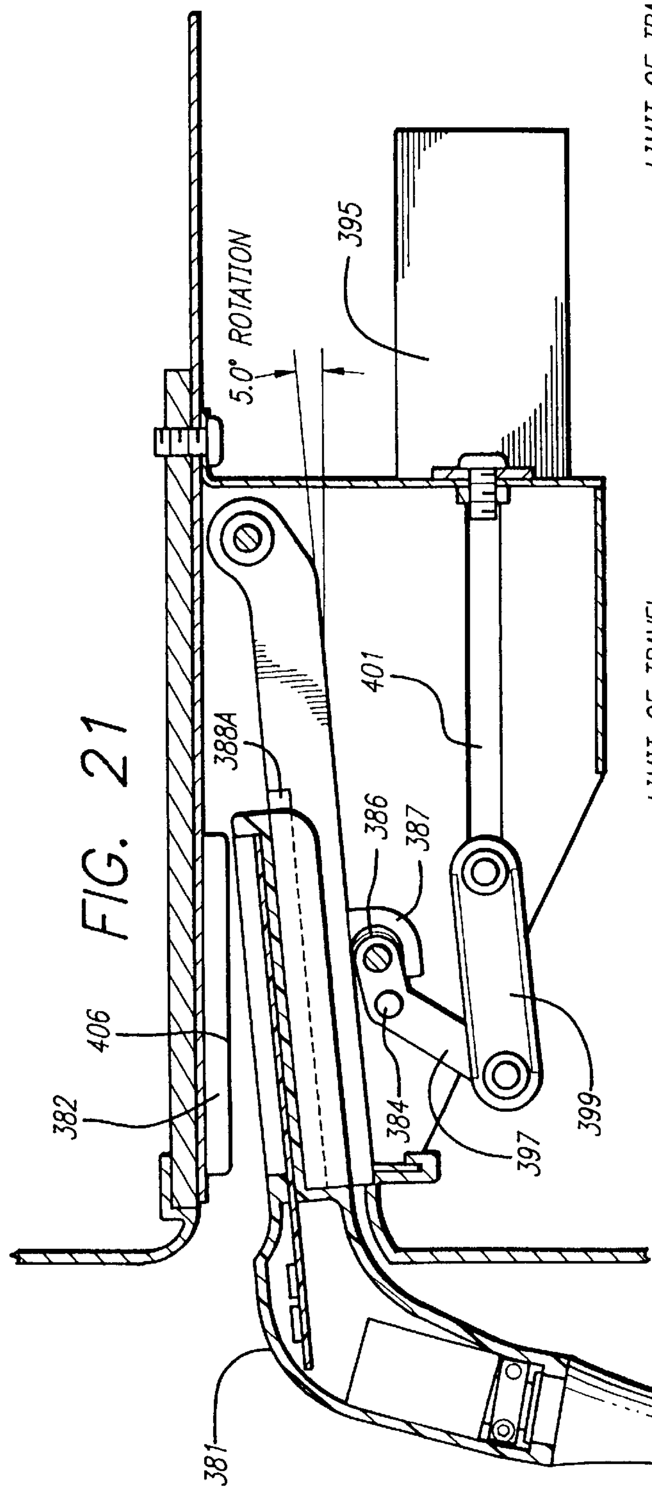
FIG. 21 is a view similar to that of FIG. 18, but with the connector unclamped from the receptacle.

The connector 381 is moved from the unclamped condition of FIG. 21 to the clamped condition of FIG. 18 by rotation of a connector actuator arm 393 in the direction of rotation indicated by numeral 388. Arm 393 is moved to the clamped position by a linear actuator 395 having a plunger 401 linearly reciprocating horizontally. A connecting linkage 399 pivotally attaches to the end of plunger 401 at one end thereof and through Torrington roller bearings 398 to an actuator link 397 which is pivotable about an actuator link pivot 384. Actuator link 397 has an actuation roller 386 journaled on a hardened pin shaft 385.

In FIG. 18, the plunger 401 is withdrawn into linear actuator 395, pulling the bottom of actuator link 97 to cause actuation roller 386 to move to the left in FIG. 18 and apply pressure to the connector actuator arm 393 to move the extension of the connector 381 upwardly for making contact with the contact nests 406 of the receptacle.

As will be appreciated by reference to FIG. 21, extending the plunger 401 out of linear actuator 395 rotates actuator link 397 clockwise as indicated by arrow 396. As actuation roller 386 moves to the right in FIG. 21, it engages the inner surface of an extraction extension 387 fixed to the connector actuator arm 393. With the plunger 401 fully extended, actuation roller 386 has moved downwardly relative to its pivot axis 384 permitting the connector 381 to be released from electrical contact with the nest plate 382 of the receptacle. To ensure that connector 381 is fully withdrawn and out of contact with nest plate 382, roller 386 pushes downwardly on the lower end of extraction extension 387. Under these circumstances, the connector 381 may be easily removed from the receptacle.

Figure 19:
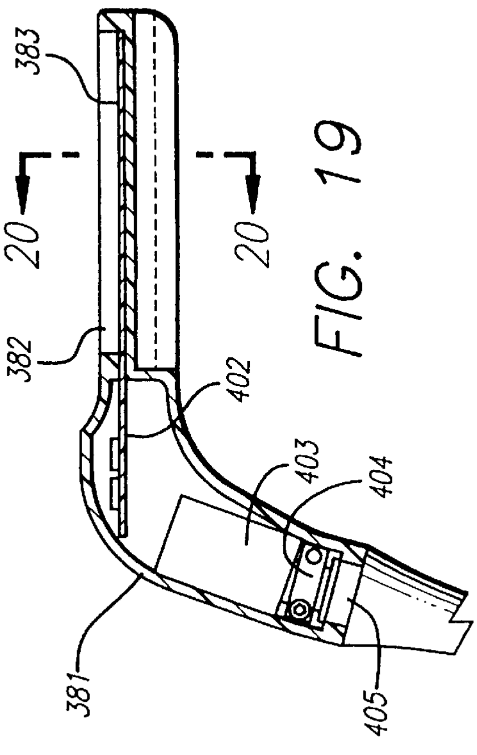
FIG. 19 is a cross-sectional view of the connector of FIG. 18.
Figure 20:
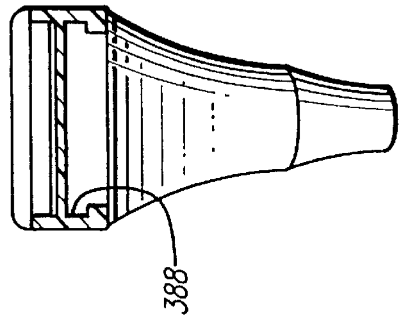
FIG. 20 is a cross-sectional view taken along the Line 20—20 of FIG. 19.

FIGS. 19 and 20 illustrate additional details of this connector 381 in which a connector printed wiring board 402 is supported in the connector body. A snap-in strain relief assembly 405 is provided at the cable entry end of the connector 381, and a standard cable clamp 404 and ferrite isolator 403 is provided.

FIG. 20 is a cross-sectional view taken along the lines 20—20 in FIG. 19 and shows a keying channel 388 which is keyed to a horizontal bar or rails 388A on the connector actuator arm 393. The engagement of bar or rails 388A in channel 388 ensures that the connector 381 will not fall out of the receptacle in the open or unlocked condition shown in FIG. 21.

Figure 22:
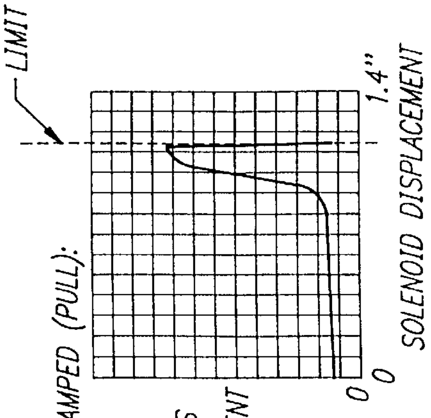
FIG. 22 is a load versus displacement graph for the clamped condition of the arrangement of FIG. 18.
Figure 23:
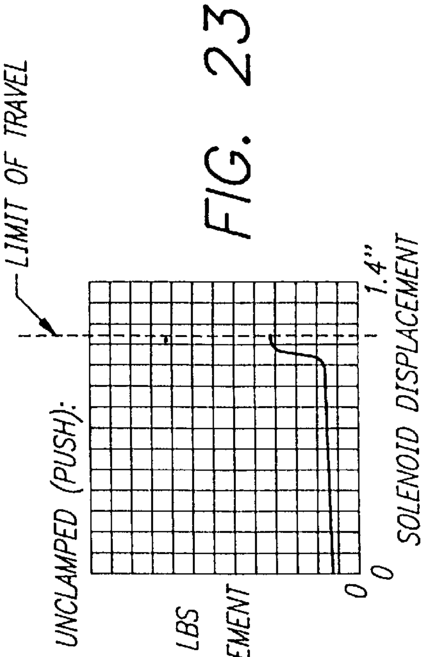
FIG. 23 is a load versus displacement graph for the unclamped condition of the arrangement of FIG. 21.
Figure 27:
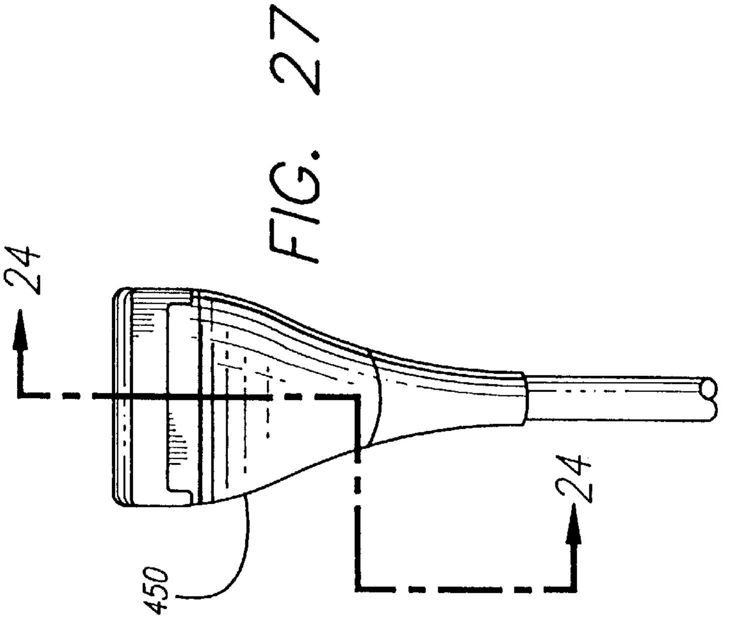
FIG. 27 is a right end view of the connector shown in FIG. 24.
Figure 25:
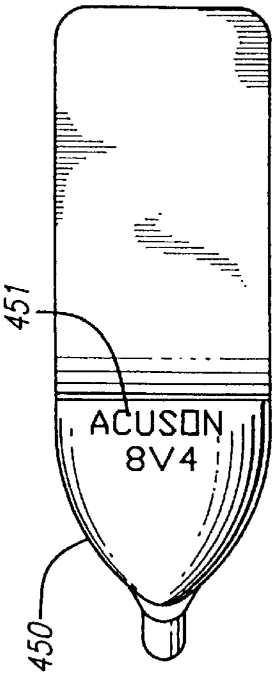
FIG. 25 is a top view of the connector of FIG. 24.
Figure 24:
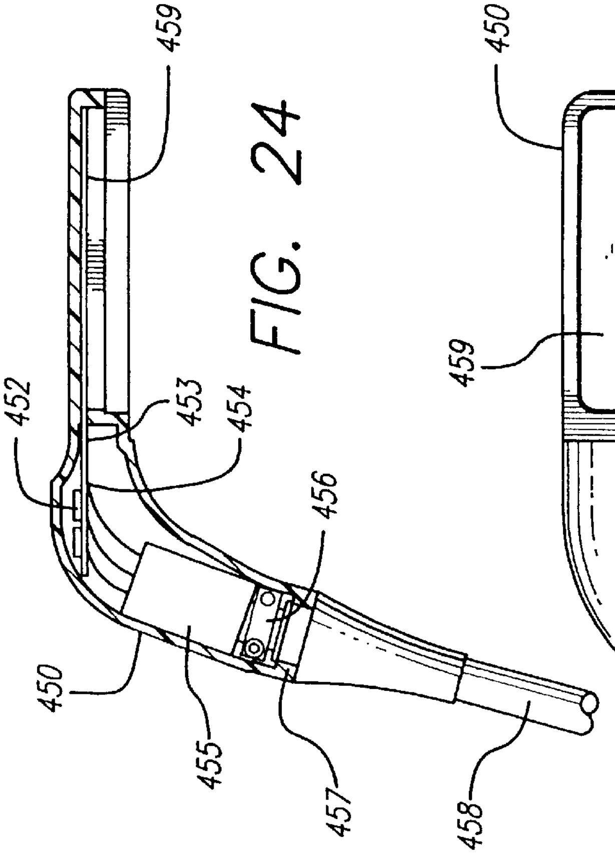
FIG. 24 is a partial cross-sectional view of another variation of an ultrasound transducer connector.
Figure 26:
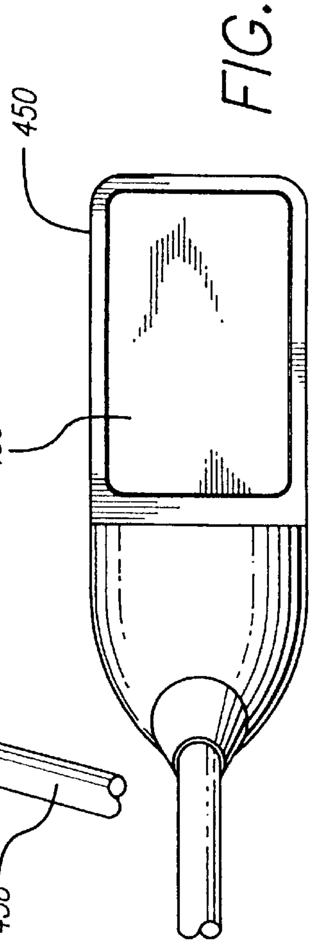
FIG. 26 is a bottom view of the connector shown in FIG. 24.

FIGS. 22 and 23 show graphs of the load requirement for the engagement of the connector printed wiring board 402 and the receptacle nest plate 382 as a function of solenoid displacement for both the clamped and unclamped condition. FIGS. 24–27 illustrate yet a further variation of an ultrasound transducer connector 450 which has lighted nomenclature 451 as shown in FIG. 25 for easy identification by the operator as to the type of transducer to which the connector is attached. The lighted nomenclature 451 is illuminated by light panels 452 powered from the ultrasound system through cable 458. As cable 458 enters the injection molded housing 457 of connector 450, it passes through a standard cable clamp 456 and a ferrite isolator 455, the coaxial conductors of the cable 458 being soldered to the printed wiring board 453 at coaxial conductor termination pads 454.

The connector pads 459, in the embodiment of the connector shown in FIGS. 24–27, face downwardly from the horizontal extension of connector 450, opposite in direction to the facing of the connector pads in the connector variation shown in FIGS. 18–21.

Figure 28:
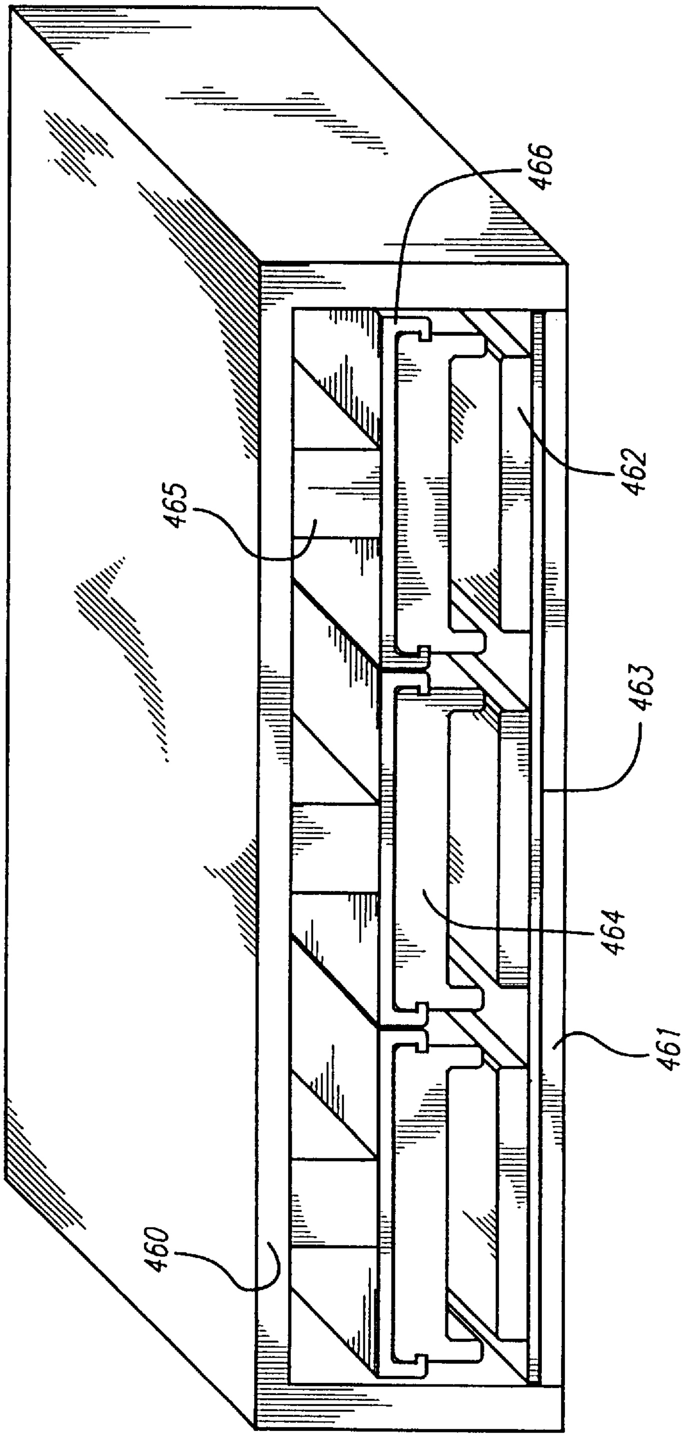
FIG. 28 depicts an alternative three-port receptacle assembly.

FIG. 28 is a basic representation of a three-port receptacle assembly provided with individual linear actuators 465 acting upon shoes 466, each shoe 466 shown to have the extension of a connector 464 mechanically held in place and ready for making contact with the nest plates 462 of the receptacle. The frame 460 provides the pressure support for the linear actuators 465 and includes a bolster plate 461 upon which the printed wiring board 463 of the receptacle is fixed. Nest plates 462 are provided in a manner similar to the already-described connector/receptacle variations.

Figure 30:
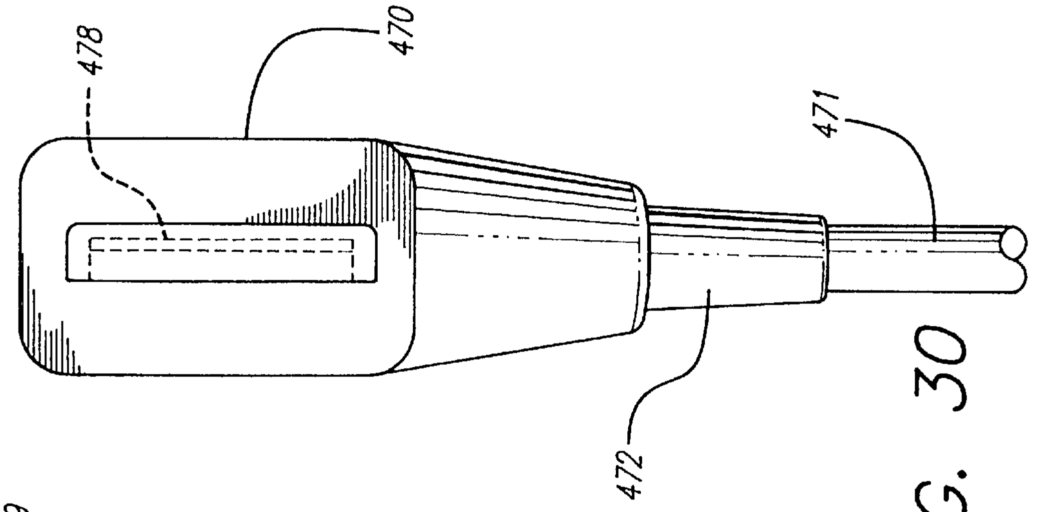
FIG. 30 is a right end view of the connector shown in FIG. 29.
Figure 29:
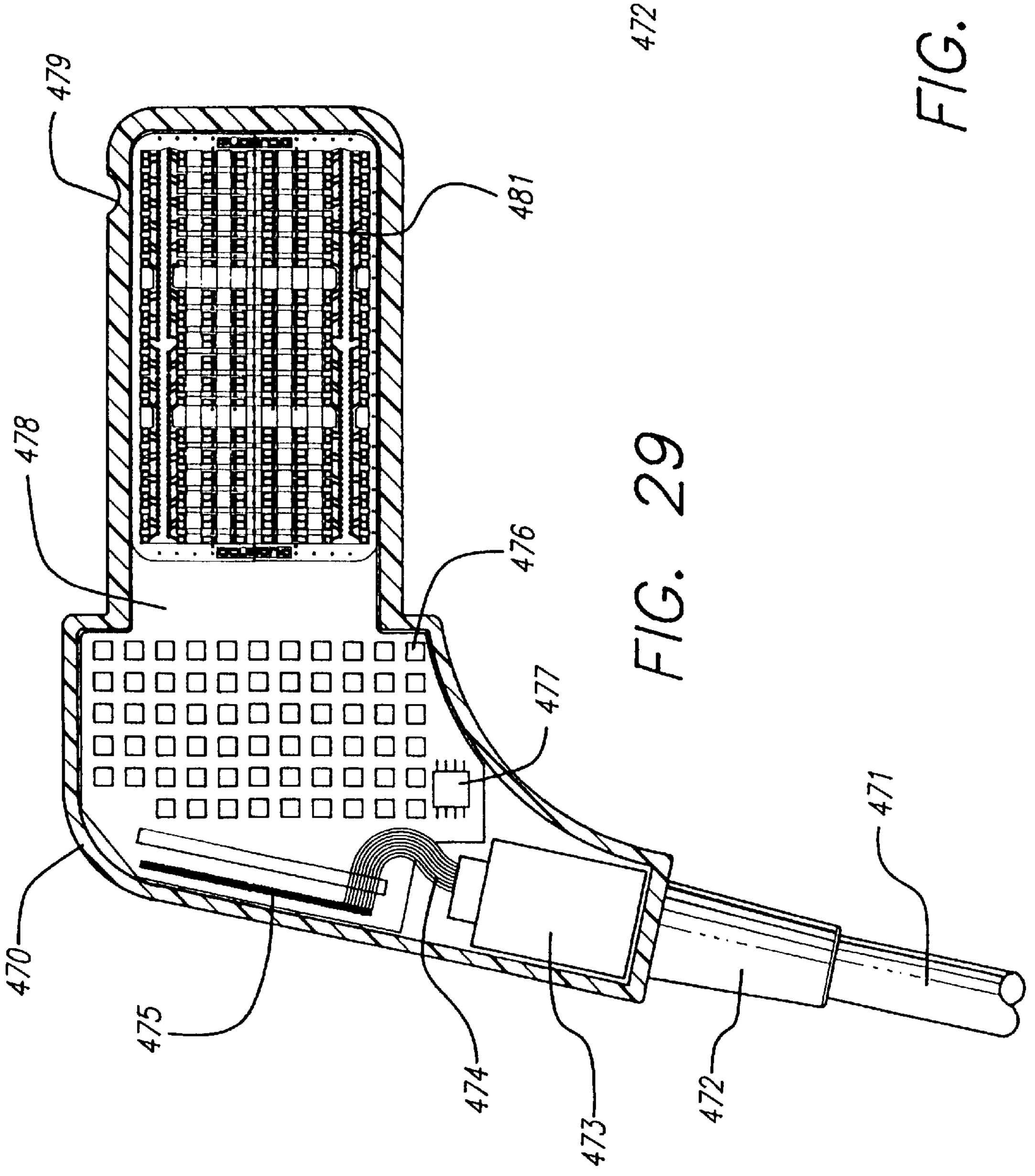
FIG. 29 is a partial cross-sectional view of a further variation of a transducer connector showing additional internal components.

FIGS. 29 and 30 illustrate yet another transducer connector 470 terminating a cable 471 through a strain relief 472 and through a ferrite isolator 473, the coaxial conductor 474 terminating at a coaxial conductor termination 475.

The connector printed wiring board 478 is provided with 64 0.1"×0.1" inductors on 0.175" centers, 64 of each such inductors placed on each side of printed wiring board 478. Inductors are frequently used in ultrasound systems to improve the energy transfer from the transducer to the imaging system, or to improve the frequency response characteristics of the transducer; other passive components such as transformers, capacitors, and resistors can be used for the same purpose. Active components can also be used; amplifiers can increase the receive signal levels for improved imaging performance, while multiplexers can allow use of imaging transducers with high channel counts (improved resolution) on imaging systems having limited channel processing capability.

A flash memory chip 477 may be provided on the printed wiring board 478. This device can be read by the imaging system; it can also be written to by the imaging system. The flash memory can be programmed during the transducer manufacturing process with such important information as the transducer identification (type of transducer), the serial number of the transducer, or any calibration or compensation information about the imaging stack. A programmable "Read Only Memory" can also be used for this transducer information.

The flash memory chip 477, or a separate flash memory chip, can also store information written to it by the imaging system. This information, which may include imaging system control settings, would decrease the amount of time required to acquire good diagnostic images the next time the transducer is used. In addition, text relating to the idiosyncrasies of the particular transducer may prove useful to other diagnosticians.

As with other connector variations described, there is provided 408 contact pads 481 accessible on one side of the connector (see FIG. 30), and a detent feature 479.

Figure 31:
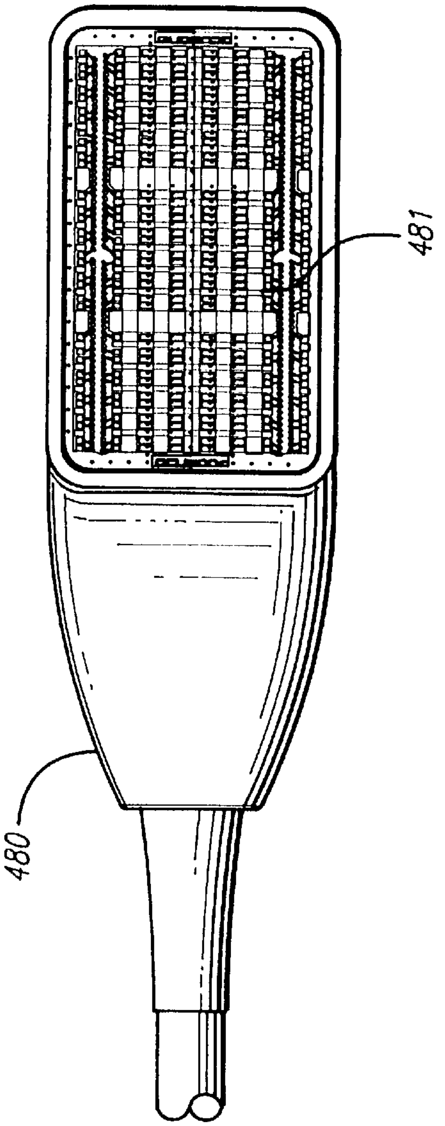
FIG. 31 is a bottom view of another transducer connector type showing the connector pads exposed.
Figure 33:
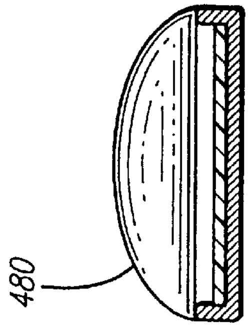
FIG. 33 is a cross-sectional view taken along the Line 33—33 in FIG. 32.
Figure 32:
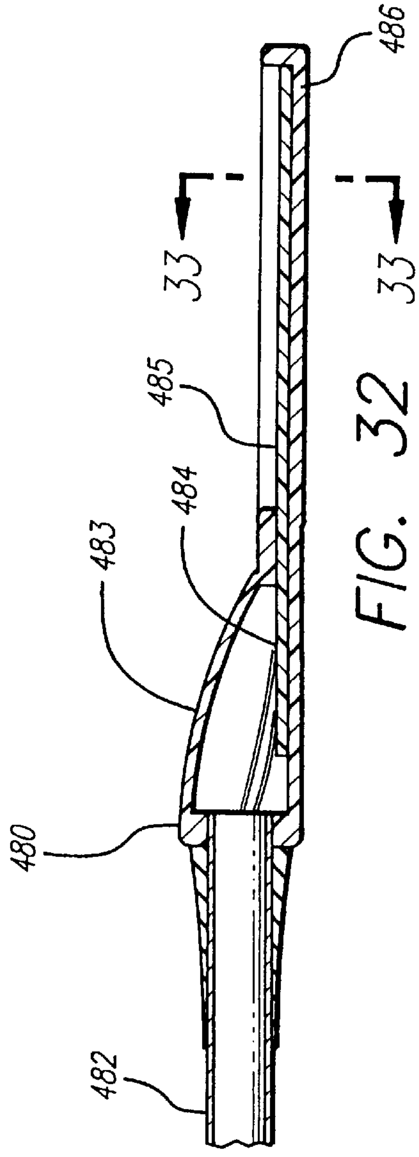
FIG. 32 is a lengthwise cross-sectional view of the connector shown in FIG. 31.

FIGS. 31–33 show yet another version of a transducer connector 480 having 408 contact pads 481 accessible on the top of the connector (see FIG. 32).

A cable 482 enters the connector 480 with the coaxial conductors terminated at 484. The plastic housing 483 of connector 480 has an oval shape portion diminishing in dimension to the extension 486 of the connector 480 at which the printed wiring board 485 is exposed for contact engagement.

Figure 35:
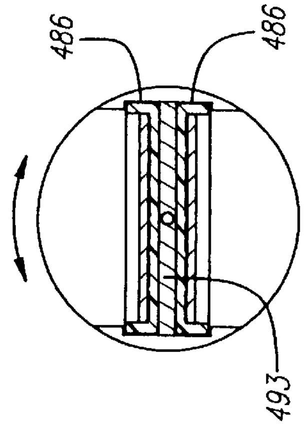
FIG. 35 is a cross-sectional view taken along the Line 35—35 in FIG. 34.
Figure 34:
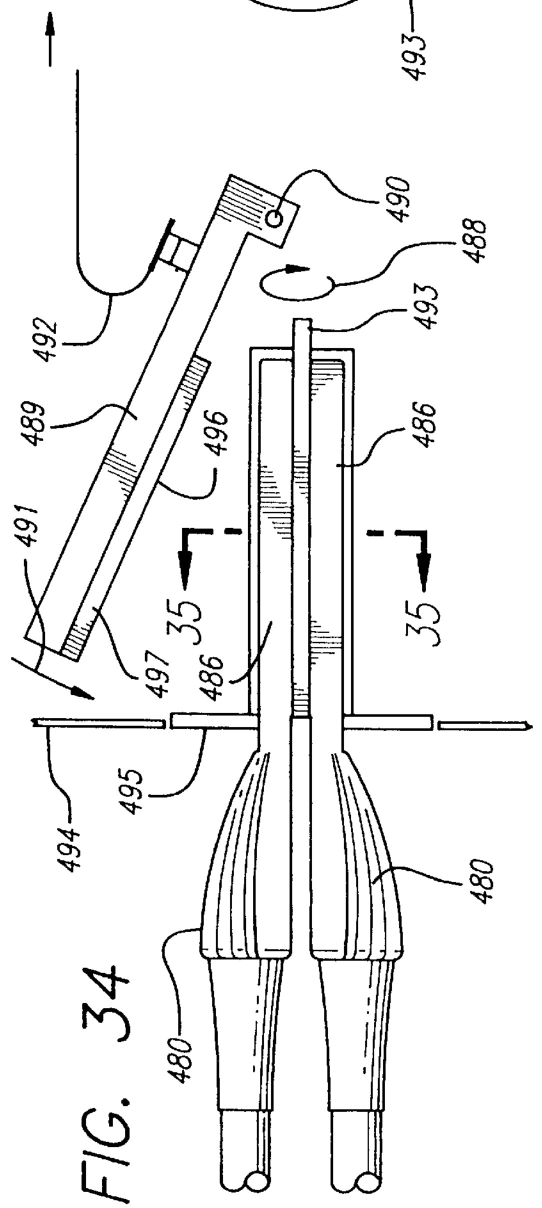
FIG. 34 is an embodiment of a rotatable dual connector arrangement using a single receptacle module.

FIGS. 34 and 35 show a mechanism for engaging the receptacle module 489 with either one of a pair of connectors 480 inserted into the receptacle opening. The connectors 480 are spaced from one another by a plate 493 which is attached to a rotating carriage 495 within imaging system front panel 494.

With the two connectors 480 inserted in the rotating carriage, the receptacle module 489 may be pivoted in the direction of arrow 491 about pivot axis 490 until the contact nests 496 of the nest plate 497 engages the printed wiring board of the top connector 480. Electrical continuity through the connector 480 to the system board is provided by a flex circuit 492.

When another connector is to be connected to the system, the receptacle module 489 is rotated upwardly, and the rotating carriage 495 is rotated as indicated by arrow 488 until the bottom connector 480 is now on the top. At this time, the system commands the receptacle module 489 to again pivot downwardly and make contact with the newly selected transducer.

Figure 36:
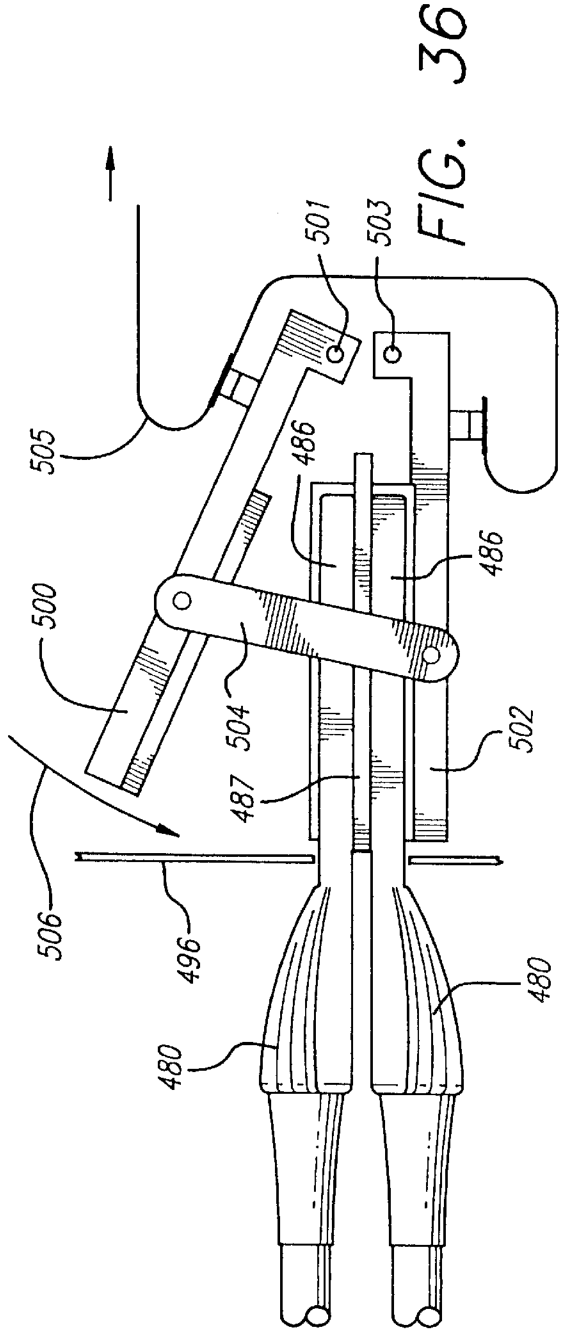
FIG. 36 is another dual connector arrangement which is rotationally fixed, and employs a pair of alternately engaged transducer modules.
Figure 37:
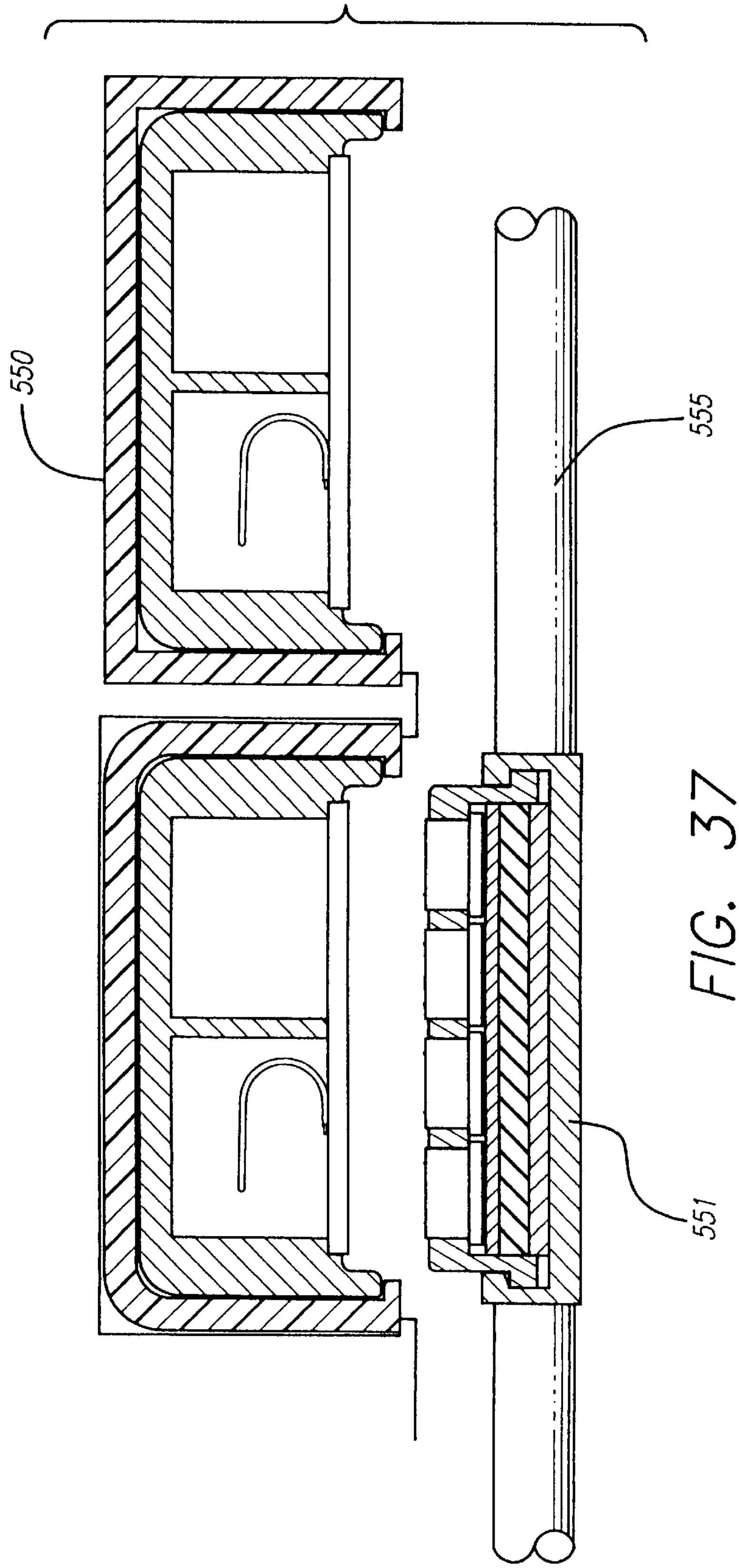
FIG. 37 is a schematic representation of a translatable receptacle module engageable with one of a number of fixed connectors.

FIG. 36 also employs a dual connector 480 arrangement in which the connectors are separated by a plate 487 and inserted into a receptacle slot in the imaging system front panel 496. In this embodiment, rather than rotating the connectors, the system receptacle is provided with a pair of receptacle modules 500 and 502. The contact nests of each receptacle module 500, 502 have their contacts wired in parallel through the flex circuit 505 leading to the system board.

As shown in FIG. 36, the bottom connector 480 is connected to the system because of the clamping of the lower receptacle module 502 to the connector extension 486 of the lower connector 480. When the upper connector is to be connected to the system, an actuator (not shown) rotates receptacle modules 500, 502 in the direction of arrow 506 about respective pivot points 501, 503, the link 504 moving the lower receptacle module 502 out of contact with the lower connector 480 and moving the upper receptacle module 500 into contact with the inserted upper connector.

Figure 40:
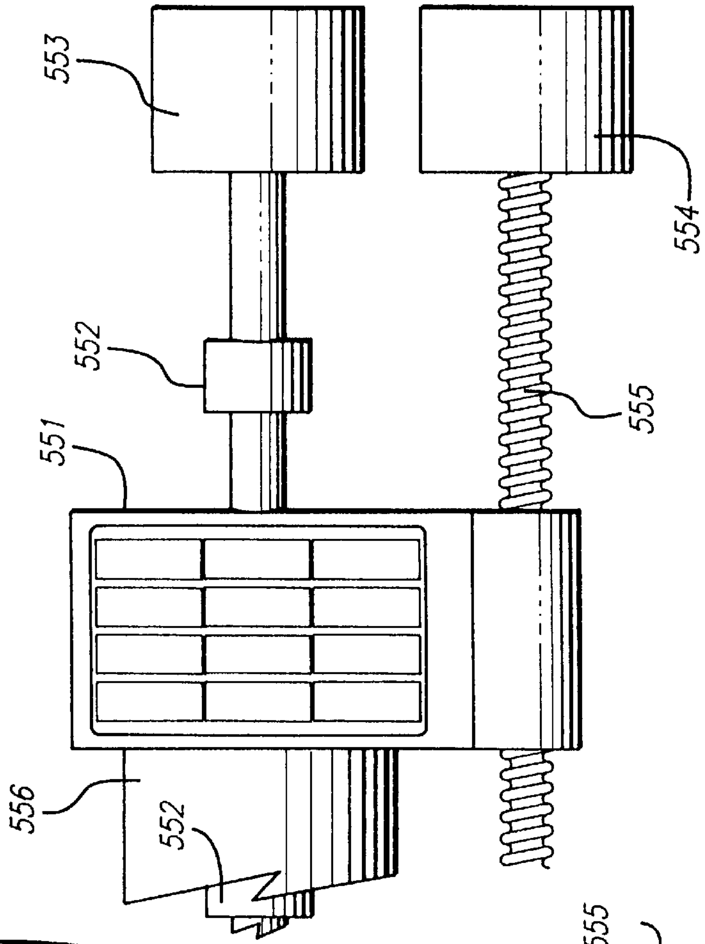
FIG. 40 is a partial schematic representation of a powered receptacle module transducer using a screw translator and a cam actuation scheme for the FIG. 37 system.
Figure 39:
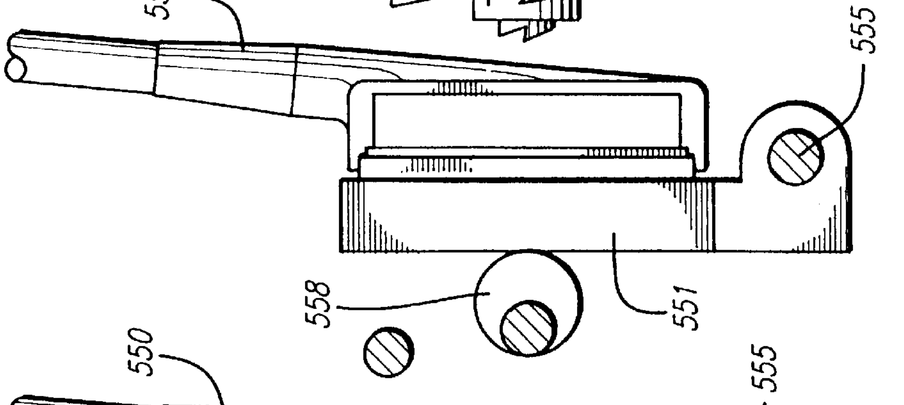
FIG. 39 is a connector/receptacle arrangement of the type used in the FIG. 37 system in the clamped condition.
Figure 38:
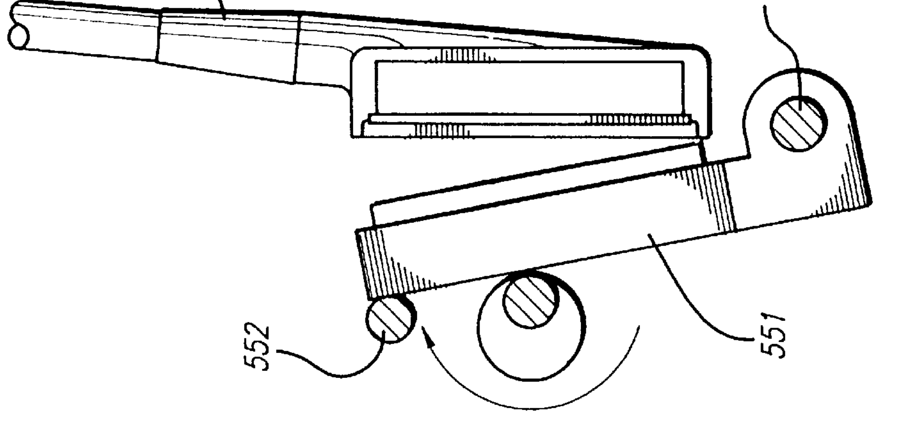
FIG. 38 is a connector/receptacle arrangement of the type used in the FIG. 37 system in the unclamped condition.

FIGS. 38–40 show an arrangement in which a series of transducer connectors 550 are arranged horizontally in fixed positions, and a moving receptacle module with appropriate contact nests is translated linearly by each of the assembled connectors and clamped to a selected one of them by a camming action. In FIG. 38, a receptacle module 551 is out of contact with the connector 550 and resting against a stop 552. FIG. 39 shows the rotation of the pin 558 in a direction to pivot the receptacle module 551 about a screw 555 and into contact with the connector 550.

A flex circuit 556 connected to the receptacle module 551 permits module 551 to be translated linearly across a number of selectable transducer connectors, e.g. a series of six transducer connectors, under software control.

A cam 552 may be provided adjacent each connector placement position, and a stepping motor 554 rotates screw 555 to translate receptacle module 551 linearly, module 551 having female threads corresponding to the male threads of screw 555.

Another stepper motor or geared motor 553, under software control of the imaging system, rotates a cam set 552 which are angularly aligned in parallel, i.e. stepper/gear motor 553 selectively rotates the cam 552 to only one of two positions, a clamped position and an unclamped position. The clamped position is selected when the receptacle module 551 is translated to a new connector position, and when that selected transducer is used, the cam 552 is rotated to depress the receptacle module 551 into contact with the printed wiring board of the selected connector.

Figure 42:
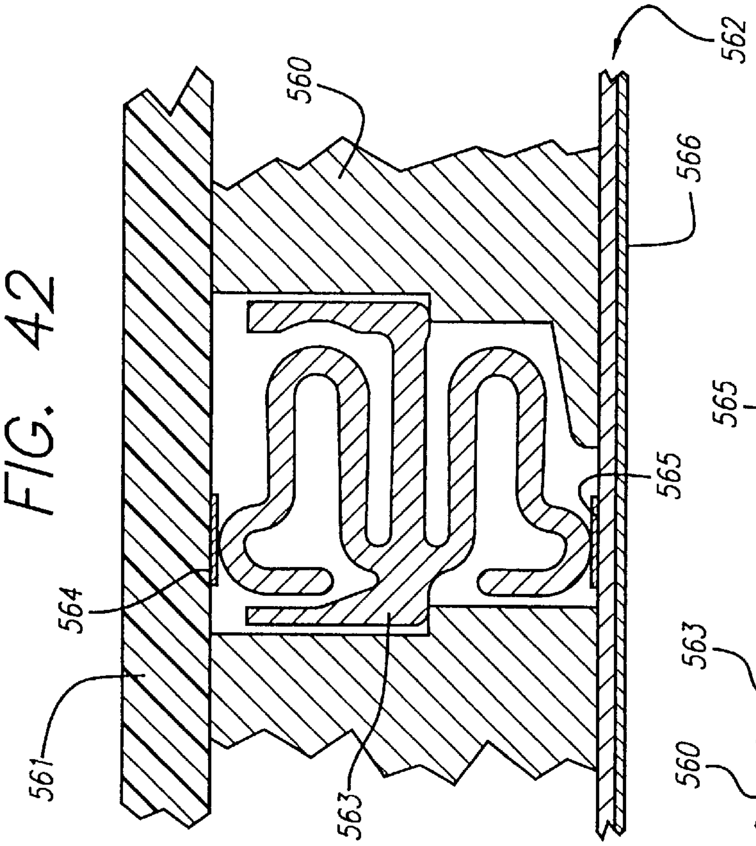
FIG. 42 is a partial cross sectional view of the arrangement depicted in FIG. 41, taken along the line 42—42 in FIG. 41.
Figure 41:
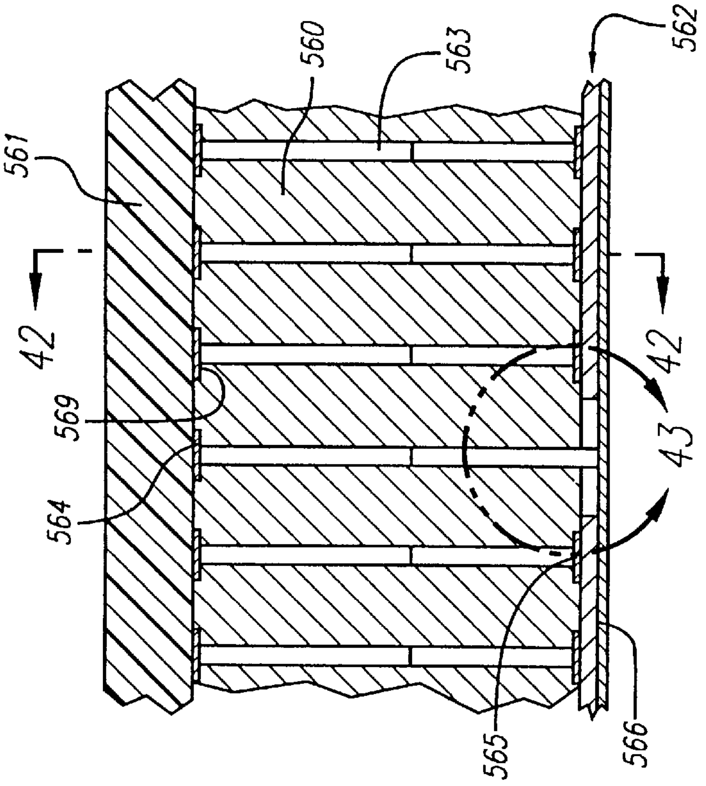
FIG. 41 is a partial cross sectional view of a connection arrangement using a contact nest connecting a receptacle to a flex circuit of an imaging system.
Figure 43:
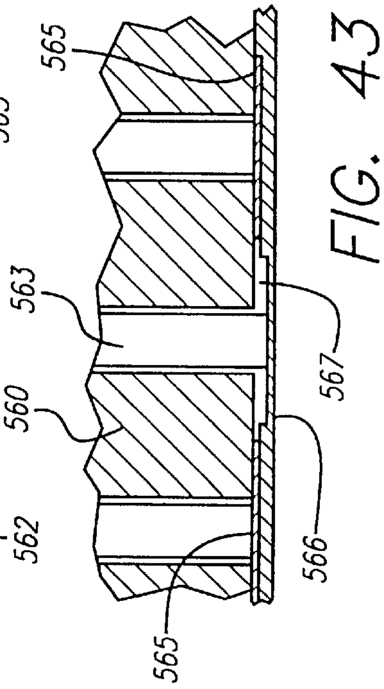
FIG. 43 is a magnified view of the lower portion of the cross sectional view enclosed within the line 43 in FIG. 41.

Shown in FIGS. 41–43 are partial cross sections of a connection arrangement using a contact nest 560 connecting the contacts 564 of a receptacle printed wiring board 561 to a flex circuit 562 of an imaging system. FIG. 42 is a partial cross sectional side view of the arrangement depicted in FIG. 41, taken along the line 42—42 in FIG. 41 and showing a spring contact 563. Contact 563 is shown to make sliding electrical contact with printed wiring board contacts 564 on the receptacle printed wiring board 561 and signal contacts 565 on the top side of flex circuit 562.

FIG. 43 is a magnified view of the lower portion of the cross sectional view enclosed within the line 43 in FIG. 41. Using a two-sided flex circuit 562, FIG. 43 shows a way of connecting ground contacts 569 with a ground plane 566 on the bottom side of flex circuit 562. This is made possible by providing an aperture 567 through the flex circuit exposing the ground plane 566 through the aperture 567. The spring contacts 563 are sufficiently resilient that good and reliable electrical connections are made at both the signal contacts 565 and the ground plane 566 due to the thin dielectric of the flex circuit between. It should be noted that either a flexible circuit or a printed wiring board can be used in the receptacle assembly, and that the showing of a printed wiring board 561 is exemplary only.

By this scheme, the contacts assigned to signals are contact pads 565 on the top side of the flex circuit 562, and those contacts 569 assigned to ground contact the ground plane 566 on the bottom side of the flex circuit 562 through apertures 567 in the flex circuit substrate. This interconnection scheme could, for example, be used in making the multi-path connections between the printed wiring board 37 of connectors 21A–21C and the flex circuit 41 through contact nest 25 in FIG. 2.

It will be understood that the apertures 567 could be formed to provide access to the signal contacts 565 through the substrate 561, but the former configuration is preferred with the aperture(s) exposing the groung contact(s) through the substrate 561.

While only certain embodiments of the invention have been set forth above, alternative embodiments and various modifications will be apparent from the above description and the accompanying drawing to those skilled in the art. For example, imaging system operator control settings may be stored in a flash memory in the connector. When initializing a transducer, this information is read by the imaging system. When switching to that transducer in the future, the previous settings are restored by the imaging system, reducing the time required to acquire diagnostically useful images. Additionally, operator inputted information may be stored in a flash memory for use by other operators or to enable recall of special information aabout the idiosyncrasies of the transducer. These and other alternatives are considered equivalents and within the spirit and scope of the present invention.

What is claimed is:

1. An ultrasound transducer connector and multiport ultrasound imaging system receptacle arrangement, comprising:

a plurality of ultrasound imaging system receptacles, each having a set of receptacle contacts;

a plurality of ultrasound transducer connectors insertable in respective ones of said receptacles, each said connector having a set of connector contacts arranged to electrically contact a corresponding set of receptacle contacts when said connector is received in and engaged by one of said receptacles; and an engagement actuator for electrically engaging only one connector by the receptacle into which it is inserted.

2. The connector and receptacle arrangement as claimed in claim 1, comprising a transducer-in-use detector, responsive to a transducer being used, to automatically enable said engagement actuator to engage a receptacle exclusively with the connector of the transducer being used.

3. The connector and receptacle arrangement as claimed in claim 2, wherein:

said transducer-in-use detector produces a transducer-in-use signal for each transducer being used; and said transducer-in-use detector comprises a priority monitor for enabling said engagement of a receptacle with the transducer being used only if all other transducers having their connectors inserted in said multiport receptacle are not being used.

4. The connector and receptacle arrangement as claimed in claim 2, comprising a transducer cable-connected to each said transducer connector, and wherein said transducer-in-use detector comprises:

a proximity detector responsive to the proximity of a human body part being in close proximity to said transducer, said proximity detector being sensitive to the change of capacitive coupled electromagnetic energy from said body part to a conductor in said transducer for generating said transducer-in-use signal.

5. The connector and receptacle arrangement as claimed in claim 4, wherein said capacitive coupled electromagnetic energy is the effect of alternating currents being picked up by the human body acting as an antenna.

6. The connector and receptacle arrangement as claimed in claim 4, wherein said transducer-in-use detector comprises:

an RF generator producing a reference signal;

a send line routing said reference signal to a first electrode in said transducer;

a return line connected to said second electrode in said transducer, said second electrode placed adjacent said first electrode; and a comparator for comparing a change in the difference between the level of said reference signal and the level of signal on said return line, said transducer-in-use signal being generated when the level in said return line increases due to said body part coupling electromagnetic energy from said first electrode to said second electrode.

7. The connector and receptacle arrangement as claimed in claim 1 comprising a receptacle panel having a plurality of elongated slots formed therein, and wherein:

said receptacles are elongated and positioned behind respective aligned ones of said slots in said panel;

each of said connectors has an elongated plug-in portion aligned with the slot and receptacle into which it is inserted; and said slots are vertically oriented and horizontally spaced apart.

8. The connector and receptacle arrangement as claimed in claim 1 comprising a receptacle panel having a plurality of elongated slots formed therein, and wherein:

said receptacles are elongated and positioned behind respective aligned ones of said slots in said panel;

each of said connectors has an elongated plug-in portion aligned with the slot and receptacle into which it is inserted; and said slots are horizontally oriented and vertically spaced apart.

9. The connector and receptacle arrangement as claimed in claim 1, wherein said engagement actuator comprises a separate contact moving member for each said receptacle selectively bringing the connector and receptacle contact sets into mutual engagement.

10. The connector and receptacle arrangement as claimed in claim 9, wherein said engagement actuator comprises a powered driver for each of said separate contact moving members.

11. The connector and receptacle arrangement as claimed in claim 10, wherein said contact moving member is adapted to move said connector contact set into and out of engagement with the contact set of the receptacle into which it is inserted.

12. The connector and receptacle arrangement as claimed in claim 10, wherein said contact moving member is adapted to move said receptacle contact set into and out of engagement with the contact set of the inserted connector.

13. The connector and receptacle arrangement as claimed in claim 10, comprising a manual release actuator, accessible externally of each said receptacle, for manually separating an engaged connector and receptacle independent of the operating state of said engagement actuator.

14. The connector and receptacle arrangement as claimed in claim 9, wherein said engagement actuator comprises a single powered driver and a common actuator member spanning across all said receptacles, said common actuator member comprising a set of operating members, each operating member positioned to effect exclusive contact engaging movement of the contact moving member with which it is associated.

15. The connector and receptacle arrangement as claimed in claim 14, wherein said common actuator member is a rotatable actuator shaft, and said operating members are cams rotatable with rotation of said actuator shaft.

16. The connector and receptacle arrangement as claimed in claim 1, comprising a latch for each connector and receptacle combination, said latch holding a connector in a receptacle and resisting withdrawal of said connector after insertion into said receptacle and before engagement of said connector and receptacle contact sets.

17. The connector and receptacle arrangement as claimed in claim 1, wherein:

each said connector comprises a printed wiring board portion having said set of connector contacts formed as contact pads exposed on a surface thereof;

each said receptacle comprises a contact nest having a first set of contacts exposed on a first surface thereof defining said set of receptacle contacts, and a second set of contacts on a second surface thereof for electrical connection with ultrasound imaging system electronics, each of said first set of nest contacts being connected to corresponding ones of said second set of nest contacts.

18. The connector and receptacle arrangement as claimed in claim 17, comprising a multi-conductor flex circuit having conductor traces in electrical contact with aligned ones of said second set of contacts of said contact nest.

19. The connector and receptacle arrangement as claimed in claim 18, wherein:

said flex circuit has said conductor traces on a first surface thereof and a ground plane on a second surface thereof, said conductor traces and said ground plane being separated by a dielectric layer;

said receptacle contact includes signal carrying contacts and ground contacts; and said contact nest comprises resilient contact connections between said first and second nest contact sets, said signal carrying contacts being aligned for engagement with said conductor traces, and said ground contacts being aligned for engagement with said ground plane through apertures formed in said dielectric layer.

20. The connector and receptacle arrangement as claimed in claim 17, comprising a multi-conductor printed wiring board having conductor traces in electrical contact with aligned ones of said second set of contacts of said contact nest.

21. The connector and receptacle arrangement as claimed in claim 20, wherein:

said printed wiring board has said conductor traces on a first surface thereof and a ground plane on a second surface thereof, said conductor traces and said ground plane being separated by a dielectric layer;

said receptacle contact includes signal carrying contacts and ground contacts; and said contact nest comprises resilient contact connections between said first and second nest contact sets, said signal carrying contacts being aligned for engagement with said conductor traces, and said ground contacts being aligned for engagement with said ground plane through apertures formed in said dielectric layer.

22. The connector and receptacle arrangement as claimed in claim 1, wherein each said receptacle comprises at least one conducting element positioned to electrically engage an exposed conductor on an inserted connector, independent of whether or not said receptacle engages said inserted connector.

23. The connector and receptacle arrangement as claimed in claim 22, wherein said exposed conductor on said connector is a ground plane.

24. The connector and receptacle arrangement as claimed in claim 22, wherein engagement of said at least one conducting element with an exposed conductor on an inserted connector develops a transducer-in-use signal for use by an ultrasound imaging system to identify which transducer is being used.

25. The connector and receptacle arrangement as claimed in claim 1, wherein each said receptacle comprises:

a connector-engaged detector for sensing whether or not said engagement actuator has effected engagement between said receptacle and an inserted connector.

26. The connector and receptacle arrangement as claimed in claim 1, wherein said engagement actuator comprises a reversible driver for applying positive force to both engage a receptacle with an inserted connector and to disengage a receptacle from an inserted connector.

27. An ultrasound transducer connector and multiport ultrasound imaging system receptacle arrangement, comprising:

a plurality of ultrasound imaging system receptacles, each having a set of receptacle contacts;

a plurality of ultrasound transducers, each having a connector with a set of connector contacts, said plurality of connectors being insertable into said plurality of receptacles without mutually engaging said set of receptacle contacts with said set of connector contacts; and an actuator, responsive to a transducer being used, for automatically electrically engaging the set of connector contacts of the transducer being used with the receptacle contacts of the receptacle into which the connector of the transducer being used is inserted.

28. The ultrasound transducer connector and multiport ultrasound imaging system receptacle arrangement as claimed in claim 27, comprising a sensor coupled to each of said receptacles, each said sensor detecting the presence of a transducer connector inserted into the associated receptacle and producing an actuation enable signal, to which said actuator is responsive, for engaging the set of connector contacts of the transducer being used with the receptacle contacts of the receptacle into which the connector of the transducer being used is inserted.

29. An ultrasound transducer connector and multiport ultrasound imaging system receptacle arrangement, comprising:

a plurality of imaging system receptacles, each having a set of receptacle contacts, the contacts of all receptacles being connected in parallel;

a plurality of ultrasound transducer connectors insertable in respective ones of said receptacles, each having a set of connector contacts arranged to electrically contact a corresponding set of receptacle contacts when said connector is received in and engaged by one of said receptacles; and a connector selector for electrically engaging the set of connector contacts of any one of the connectors with the set of receptacle contacts of the receptacle into which it is inserted.

30. The ultrasound transducer connector and multiport ultrasound imaging system receptacle arrangement as claimed in claim 28, comprising:

a transducer-in-use detector for enabling said connector actuator to engage said one connector with said receptacle into which it is inserted when a transducer associated with said one connector is being used; and a manual transducer selector for enabling said connector selector to engage said one connector with said receptacle into which it is inserted.

31. The ultrasound transducer connector and multiport ultrasound imaging system receptacle arrangement as claimed in claim 30, comprising:

a manual/automatic switch having a manual position and an automatic position, said manual/automatic switch disconnecting said transducer-in-use detector when in said manual position.

32. The ultrasound transducer connector and multiport ultrasound imaging system receptacle arrangement as claimed in claim 30, comprising:

a manual/automatic switch having a manual position and an automatic position, said manual/automatic switch disconnecting said transducer-in-use detector when in said manual position, and disconnecting said manual transducer selector when in said automatic position.

33. An ultrasound transducer connector and receptacle arrangement, comprising:

an imaging system receptacle having a set of receptacle signal contacts on a first surface of a receptacle substrate, and further having at least one receptacle ground contact on a second surface of said substrate, said second surface spaced from said first surface, said substrate having at least one aperture therein providing access to one of said set of receptacle signal and ground contacts through said substrate;

an ultrasound transducer connector insertable in said receptacle, said connector having a set of connector contacts arranged to electrically contact a corresponding set of receptacle signal and ground contacts when said connector is received in and is electrically engaged by one of said receptacles, said receptacle being coupled to an actuator which provides electrical engagement responsive to a transducer being used a contact nest comprising a plurality of resilient contacts interconnecting said set of receptacle contacts with said set of connector contacts.

34. The ultrasound transducer connector and receptacle arrangement as claimed in claim 33, wherein said at least one aperture provides access to said at least one ground contact through said substrate.

35. An ultrasound transducer connector and receptacle arrangement, comprising:

an imaging system receptacle having a set of receptacle contacts on a first surface of a receptacle substrate;

an ultrasound transducer connector insertable in said receptacle, said connector having a set of connector contacts arranged to electrically contact a corresponding set of receptacle contacts when said connector is received in and electrically engaged by one of said receptacles;

a contact nest comprising a plurality of resilient contacts for interconnecting said set of receptacle contacts with said set of connector contacts; and interengaging raised frames around the sets of contacts on said connector and said receptacle to align said set of receptacle contacts with respect to said set of connector contacts when said connector and receptacle are interconnected.

36. An ultrasound transducer connector and receptacle arrangement, comprising:

an imaging system receptacle mounted on a receptacle frame and having a set of receptacle contacts on a first surface of a receptacle substrate;

an ultrasound transducer connector insertable in said receptacle, said connector having a set of connector contacts arranged to electrically contact a corresponding set of receptacle contacts when said connector is received in and engaged by one of said receptacles, said receptacle being coupled to an actuator which provides electrical engagement responsive to a transducer being used;

a contact nest comprising a plurality of resilient contacts for interconnecting said set of receptacle contacts with said set of connector contacts; and a contact nest hinge for pivoting said contact nest with respect to said receptacle frame, resulting in a tangential motion of said receptacle contacts with respect to said connector contacts.

37. An ultrasound transducer connector and multiport ultrasound imaging system receptacle arrangement, comprising:

an ultrasound imaging system receptacle having a set of receptacle contacts, said receptacle comprising a contact nest assembly having a first set of contacts exposed on a first surface thereof defining said set of receptacle contacts, and a second set of contacts on a second surface thereof for electrical connection with ultrasound imaging system electronics, each of said first set of nest contacts being connected to corresponding ones of said second set of nest contacts;

a plurality of ultrasound transducer connectors each engageable with said receptacle, each said connector having a set of connector contacts arranged to be electrically coupled to corresponding ones of said set of receptacle contacts when said connector and receptacle are interengaged, each said connector comprising a printed wiring board portion having said set of connector contacts formed as contact pads exposed on a surface thereof; and an engagement actuator for exclusively engaging only one connector with the receptacle, said engagement actuator comprising a stepper motor and lead screw cam for translating said receptacle contact nest to one of a plurality of receptacle positions, one of said connectors being located at each said receptacle position.

38. The ultrasound transducer connector and multiport ultrasound imaging system receptacle arrangement as claimed in claim 35, comprising:

a flex circuit carrying signals from the translatable nest assembly to an imaging system.

* * * * *